US012642871B2

(12) United States Patent
Liu et al.

(10) Patent No.: US 12,642,871 B2
(45) Date of Patent: Jun. 2, 2026

(54) LYOPHILIZED FORMULATIONS OF AAV DRUG PRODUCTS

(71) Applicant: Regeneron Pharmaceuticals, Inc., Tarrytown, NY (US)

(72) Inventors: Dingjiang Liu, Pleasantville, NY (US); Li Zhi, Tarrytown, NY (US); Yao Chen, Whitestone, NY (US); Kuan-Yu Lai, Livingston, NJ (US); Jonathan Wert, Yorktown Heights, NY (US); Xiaoyan Wang, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 482 days.

(21) Appl. No.: 18/120,762

(22) Filed: Mar. 13, 2023

(65) Prior Publication Data

US 2023/0293724 A1     Sep. 21, 2023

Related U.S. Application Data

(60) Provisional application No. 63/319,657, filed on Mar. 14, 2022.

(51) Int. Cl.
| | |
|---|---|
| *A61K 35/76* | (2015.01) |
| *A61K 9/16* | (2006.01) |
| *A61K 9/19* | (2006.01) |
| *A61K 47/18* | (2017.01) |
| *A61K 47/26* | (2006.01) |
| *A61K 48/00* | (2006.01) |

(52) U.S. Cl.
CPC ........ *A61K 48/0041* (2013.01); *A61K 9/1617* (2013.01); *A61K 9/1623* (2013.01); *A61K 9/1641* (2013.01); *A61K 9/19* (2013.01); *A61K 35/76* (2013.01)

(58) Field of Classification Search
None
See application file for complete search history.

(56) References Cited

U.S. PATENT DOCUMENTS

| | | | | |
|---|---|---|---|---|
| 2012/0121580 A1* | 5/2012 | Bhambhani | .............. | A61K 9/19 |
| | | | | 424/130.1 |
| 2021/0123028 A1* | 4/2021 | Knop | ..................... | A61K 47/26 |

FOREIGN PATENT DOCUMENTS

| | | | | | |
|---|---|---|---|---|---|
| WO | WO-2016087457 A1 * | 6/2016 | .............. | A61P 31/12 |
| WO | 20/102369 A1 | 5/2020 | | |
| WO | 20/150556 A1 | 7/2020 | | |
| WO | WO-2020150556 A1 * | 7/2020 | .............. | A61P 25/14 |

(Continued)

OTHER PUBLICATIONS

Haeuser et al. (Abstract in: Pharmaceutics 2019, (11); 616:16 pages). (Year: 2019).*

(Continued)

*Primary Examiner* — Ernst V Arnold
(74) *Attorney, Agent, or Firm* — Schwabe, Williamson & Wyatt PC; David Mellman

(57) ABSTRACT

The present disclosure provides stable lyophilized pharmaceutical compositions comprising recombinant adeno-associated virus (rAAV) particles. In certain embodiments, the compositions contain, in addition to the rAAV particles, a buffer, one or more salts, a surfactant, a bulking agent, and a sugar. The pharmaceutical compositions of the present disclosure exhibit a substantial degree of rAAV stability upon stress and storage.

20 Claims, 14 Drawing Sheets

(56) References Cited

FOREIGN PATENT DOCUMENTS

| WO | WO-2020176614 A1 * | 9/2020 | .............. A61P 21/00 |
|----|--------------------|--------|----------------------------|
| WO | 20/214929 A1 | 10/2020 | |
| WO | WO-2020214929 A1 * | 10/2020 | ............ A61K 47/34 |
| WO | 21/071835 A1 | 4/2021 | |
| WO | 21/202943 A1 | 10/2021 | |

OTHER PUBLICATIONS

Demattia et al. (Journal of Viralogy 2012;86(12):6947-6958) (Year: 2012).*

Wlodarczyk et al. (European Journal of Pharmaceutics and Biopharmaceutics 2018; 131:92-98) (Year: 2018).*

WIPO Application No. PCT/US2023/015112, PCT International Search Report and Written Opinion of the International Searching Authority mailed Jun. 5, 2023.

U.S. Appl. No. 63/319,657, filed Mar. 14, 2022, Expired.

PCT/US2023/015112, Mar. 13, 2023, Pending.

* cited by examiner

Full Capsid

Partial Capsid

Empty Capsid

AAV Capsid

Therapeutic gene

Formulation:    BA1    BA2

| Formulation | Base Formulation | NaCl | L-Arg HCl | MgCl₂ |
|---|---|---|---|---|
| Optimized Formulation (control) | 10 mM Tris, 5% sucrose, 3.3% mannitol, 0.01% P188, pH 7.3 | 30mM | 80mM | 0 |
| F8 | | 80 mM | 0 | 0 |
| F9 | | 40 mM | 40 mM | 0 |
| F10 | | 80 mM | 0 | 2 mM |

FIG. 9A

LYOPHILIZED FORMULATIONS OF AAV DRUG PRODUCTS

CROSS-REFERENCE TO RELATED APPLICATION

This application claims the benefit under 35 USC § 119(e) of U.S. Provisional Application No. 63/319,657, filed Mar. 14, 2022, which is incorporated herein by reference in its entirety for all purposes.

FIELD OF THE INVENTION

The present invention relates to stable lyophilized compositions of recombinant adeno-associated virus (rAAV) products, and to methods for producing such compositions.

BACKGROUND

In recent years, gene therapy has drawn tremendous interest among biopharmaceutical companies, and has emerged as a transformational strategy that can provide new treatment options for numerous genetic diseases. This is attributed to the advances in virology, immunology, vector engineering technology, vector manufacturing sciences, and other related areas which continued to provide improved vectors that overcame the safety issues associated with early gene delivery vectors such as retroviruses Currently, there are more than 700 ongoing or completed gene therapy clinical trials worldwide. Adeno-associated virus (AAV), which is a non-enveloped, single-stranded DNA virus, has emerged as an attractive class of therapeutic agents to deliver genetic materials to host cells for gene therapy, due to its ability to transduce a wide range of species and tissue in vivo, low risk of immunotoxicity, and mild innate and adaptive immune responses.

AAV gene therapy products are typically administered by injection, and are formulated as liquid solutions and stored frozen at low temperatures (e.g., below −65° C.). For any injectable, liquid formulation is usually the preferred dosage form because it is easier to manufacture and convenient for end-users. However, maintaining stability for AAV products in an aqueous environment can be challenging due to poor structure stability. Thus, freezing is commonly used to improve the long-term storage stability for AAV by minimizing the rate of degradation due to both physical and chemical instability, but freezing presents practical challenges for supply chain and inventory management. In a typical drug product (DP) manufacturing process, AAV can be exposed to freeze-thaw when the drug substance (DS) is stored frozen and is thawed prior to preparing for DP fill-finish. A minimum of one freeze-thaw is also necessary prior to administration of AAV DP in the clinic. Short-term storage of AAV in the liquid state under ambient conditions is required during DP manufacturing processes, subsequent packaging and labeling, as well as in clinical applications. Product degradation, such as aggregation of AAV or loss of titer, can occur during freeze-thaw as well as extended storage at elevated temperatures. Aggregation can reduce viral titer and thus product efficacy, increase the load of potentially immunogenic viral proteins, and impact biodistribution, leading to inconsistent in vivo activity of the AAV product Therefore, maintaining stability and activity for AAV products during manufacturing and storage is critical for the successful development of AAV as a therapeutic agent.

BRIEF SUMMARY OF THE INVENTION

In one aspect, the present disclosure provides a pharmaceutical formulation comprising (i) recombinant adeno-associated virus (rAAV) particles, (ii) a buffering agent at a concentration of from about 1 mM to about 20 mM, (iii) a first salt at a concentration of from about 10 mM to about 50 mM, (iv) a second salt at a concentration of from about 20 mM to 100 mM, (v) a sugar at a concentration of from about 1% w/v to about 10% w/v, (vi) a bulking agent at a concentration of from about 1% w/v to about 6% w/v, and (vii) a surfactant at a concentration of from about 0.001% w/v to about 0.1% w/v, wherein the formulation has a pH of from about 6.8 to about 7.8.

In some embodiments, the buffering agent is a Tris buffer or a sodium phosphate buffer. In some cases, the buffering agent is a Tris buffer. In some embodiments, the concentration of the buffering agent is from 5 mM to 15 mM. In some cases, the concentration of buffering agent is 10 mM±2 mM.

In some embodiments, the first salt is sodium chloride, potassium chloride, or magnesium chloride. In some cases, the first salt is sodium chloride. In some embodiments, the concentration of the first salt is from 20 mM to 40 mM. In some cases, the concentration of the first salt is 30 mM±5 mM.

In some embodiments, the second salt is arginine hydrochloride. In some embodiments, the concentration of the second salt is from 70 mM to 90 mM. In some cases, the concentration of the second salt is 80 mM±5 mM. In some embodiments, the concentration of the second salt is from about 20 mM to about 60 mM. In some cases, the concentration of the second salt is 40 mM±5 mM. In some embodiments, the concentration of the second salt is from 30 mM to 90 mM.

In some embodiments, the sugar is sucrose or trehalose. In some cases, the sugar is sucrose. In some embodiments, the concentration of sugar is from 3% w/v to 7% w/v. In some cases, the concentration of sugar is 5% w/v±1% w/v.

In some embodiments, the bulking agent is mannitol or glycine. In some cases, the bulking agent is mannitol. In some embodiments, the concentration of the bulking agent is from 2% w/v to 5% w/v. In some cases, the concentration of the bulking agent is 3.3% w/v±0.5% w/v.

In some embodiments, the surfactant is a polysorbate or a poloxamer. In some cases, the polysorbate is polysorbate 80 (PS80). In some cases, the poloxamer is poloxamer 188 (P188). In some embodiments, the concentration of surfactant is from 0.001% w/v to 0.1% w/v. In some cases, the surfactant concentration is 0.01% w/v±0.005% w/v.

In some embodiments, the pH of the formulation is from 7.0 to 7.6. In some cases, the pH of the formulation is 7.3±0.1.

In some embodiments, the ratio of bulking agent to sugar is from 1:1 to 1:3. In some embodiments, the ratio of bulking agent to sugar is from 1:1 to 1:7. In some cases, the ratio of mannitol to sucrose is from 1:1 to 1:3. In some cases, the ratio of mannitol to sucrose is from 1:1 to 1:7. In some embodiments, the ratio mannitol to sucrose is 3.3:5. In some embodiments, the ratio of first salt to second salt is from 1:1 to 1:4. In some cases, the ratio of sodium chloride to arginine hydrochloride is 1:1 to 1:4. In some embodiments, the ratio of sodium chloride to L-arginine hydrochloride is 3:8.

In some embodiments, the formulation has a total ionic strength of from 70 mM to 120 mM. In some cases, the total ionic strength is 80 mM±5 mM. In some cases, the total ionic strength is 110 mM±10 mM.

In some embodiments, the pharmaceutical formulation comprises from 1×10E10 vg/mL to 1×10E15 vg/mL. In some cases, the pharmaceutical formulation comprises from 1×10E12 vg/mL to 1×10E14 vg/mL. In some cases, the pharmaceutical formulation comprises about 1×10E13 vg/mL.

In one aspect, the present disclosure provides a pharmaceutical formulation comprising (i) recombinant adeno-associated virus (rAAV) particles at a concentration of from 1×10E10 vg/mL to 1×10E15 vg/mL, (ii) a phosphate buffer at a concentration of from 10 mM±1 mM, (iii) sodium chloride at a concentration of 30 mM±3 mM, (iv) L-arginine hydrochloride at a concentration of 80 mM±8 mM, (v) sucrose at a concentration of 5% w/v±0.5% w/v, (vi) mannitol at a concentration of 3.3% w/v±0.3% w/v, and (vii) poloxamer 188 at a concentration of 0.005% w/v±0.001% w/v, wherein the formulation has a pH of 7.3±0.2. In some cases, the pharmaceutical formulation comprises from 1×10E12 vg/mL to 1×10E14 vg/mL. In some cases, the pharmaceutical formulation comprises about 1×10E13 vg/mL.

In one aspect, the present disclosure provides a pharmaceutical formulation comprising (i) recombinant adeno-associated virus (rAAV) particles at a concentration of from 1×10E10 vg/mL to 1×10E15 vg/mL, (ii) a Tris buffer at a concentration of 10 mM±1 mM, (iii) sodium chloride at a concentration of 30 mM±3 mM, (iv) L-arginine hydrochloride at a concentration of 80 mM±8 mM, (v) sucrose at a concentration of 5% w/v±0.5% w/v, (vi) mannitol at a concentration of 3.3% w/v±0.3% w/v, and (vii) poloxamer 188 at a concentration of 0.01% w/v±0.002% w/v, wherein the formulation has a pH of 7.3±0.2. In some cases, the pharmaceutical formulation comprises from 1×10E12 vg/mL to 1×10E14 vg/mL. In some cases, the pharmaceutical formulation comprises about 1×10E13 vg/mL.

In some embodiments, the rAAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S. In some embodiments, the rAAV particles are of serotype AAV1, AAV2, AAV3, AAV4, AAV5, AAV6, AAV7, AAV8, AAV9, or AAV10. In some cases, the rAAV particles are of serotype AAV1. In some cases, the rAAV particles are of serotype AAV5. In some cases, the rAAV particles are of serotype AAV8. In some cases, the rAAV particles are of serotype AAV9.

In some embodiments, the formulation has an average particle size of from about 20 nm to about 40 nm, as determined by dynamic light scattering.

In some embodiments, the formulation contains a collection of rAAV particles comprising at least 95% full capsids, as determined by anion-exchange chromatography.

In one aspect, the present disclosure provides a stable lyophilized pharmaceutical composition formed by lyophilizing the pharmaceutical formulation discussed above or herein.

In some embodiments, the lyophilized pharmaceutical composition has a moisture content of 1.5% or less. In some embodiments, the lyophilized pharmaceutical composition has a moisture content of 1.0% or less. In some embodiments, the lyophilized pharmaceutical composition has a moisture content of from 0.5% to 0.8%, or 0.5%, 0.55%, 0.6%, 0.65%, 0.7%, 0.75%, or 0.8%. In any of the various embodiments, the moisture content may be determined by Karl Fischer (KF) titration.

In some embodiments, the lyophilized pharmaceutical composition can be reconstituted in 30 seconds or less. In some embodiments, the lyophilized pharmaceutical composition can be reconstituted in 20 seconds or less. In some embodiments, the lyophilized pharmaceutical composition can be reconstituted in 15 seconds or less.

In one aspect, the present disclosure provides a reconstituted drug product formed by reconstituting the lyophilized pharmaceutical composition discussed above or herein.

In some embodiments, the reconstituted drug product comprises an average particle size of from about 20 nm to about 40 nm, as determined by dynamic light scattering.

In some embodiment, the reconstituted drug product comprises a collection of rAAV particles comprising at least 95% full capsids, as determined by anion-exchange chromatography. In some embodiments, the reconstituted drug product comprises a collection of rAAV particles comprising a percentage of full capsids, as determined by anion-exchange chromatography, wherein the percentage of full capsids in the reconstituted drug product is within 2% of a percentage of full capsids in the pharmaceutical formulation prior to lyophilization. In some cases, the percentage of full capsids in the reconstituted drug product is within 1% of a percentage of full capsids in the pharmaceutical formulation prior to lyophilization. In some cases, the percentage of full capsids in the reconstituted drug product is within 0.5% of a percentage of full capsids in the pharmaceutical formulation prior to lyophilization.

In some embodiments, the reconstituted drug product comprises a vector genome titer, as determined by droplet digital polymerase chain reaction, wherein the vector genome titer in the reconstituted drug product is within 10% of the vector genome titer present in the pharmaceutical formulation prior to lyophilization. In some cases, the vector genome titer in the reconstituted drug product is within 7% of the vector genome titer present in the pharmaceutical formulation prior to lyophilization.

In any of the various embodiments discussed above or herein, the reconstituted drug product may be formed by reconstituting the lyophilized pharmaceutical composition after storage for 1 month at a temperature of from 2-8° C. In some embodiments, the reconstituted drug product may be formed by reconstituting the lyophilized pharmaceutical composition after storage for 3 months at a temperature of from 2-8° C. In some embodiments, the reconstituted drug product may be formed by reconstituting the lyophilized pharmaceutical composition after storage for 6 months at a temperature of from 2-8° C.

In one aspect, the present disclosure provides a container containing the pharmaceutical formulation discussed above or herein.

In one aspect, the present disclosure provides a container containing the lyophilized pharmaceutical composition discussed above or herein.

In one aspect, the present disclosure provides a container containing the reconstituted drug product discussed above or herein.

In any of the various embodiments, the container may be a glass vial.

In one aspect, the present disclosure provides a kit comprising the container discussed above or herein, and instructions for use.

In one aspect, the present disclosure provides a method of producing the stable lyophilized pharmaceutical composition discussed above or herein, wherein the method comprises performing a lyophilization process on the pharmaceutical formulation discussed above or herein.

In some embodiments, the lyophilization process comprises (i) freezing, (ii) annealing, (iii), primary drying, and (iv) secondary drying. In some cases, the freezing is performed at a temperature of −45° C.±5° C. for a period of 60 minutes±10 minutes. In some cases, the freezing is performed both before and after the annealing. In some cases, the annealing is performed at a temperature of −20° C.±5° C. for a period of 6 hours±30 minutes. In some cases, the primary drying is performed at a temperature of −26° C.±5° C. for a period of 50 hours±10 hours. In some cases, the secondary drying is performed at a temperature of 35° C.±5° C. for a period of from 5 hours to 20 hours. In some cases, the secondary drying is performed at a temperature of 35° C.±5° C. for a period of 15 hours±5 hours.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure.

Other embodiments will become apparent from a review of the ensuing detailed description.

BRIEF DESCRIPTION OF THE DRAWINGS

FIG. 6A shows characterization of the collapse temperature Tc by freeze drying microscopy, and FIG. 6B shows the glass transition temperature Tg' by DSC in formulation F7.

FIG. 7A shows particle size analysis by DLS, FIG. 7B shows viral genome titer analysis by ddPCR, and FIG. 7C shows analysis of capsid purity by percentage of full capsid using AEX-UPLC.

Results from the pre-lyophilization formulation are illustrated with light colored dots, and results from the reconstituted post-lyophilization product are illustrated with dark colored dots. FIG. 8A shows particle size analysis by DLS, FIG. 8B shows viral genome titer analysis by ddPCR, and FIG. 8C shows analysis of capsid purity by percentage of full capsid using AEX-UPLC.

FIGS. 9A and 9B show results of salt screening for formulation preparation. FIG. 9A shows formulation compositions of a formulation (control) containing $1 \times 10^{13}$ vg/mL AAV8, 10 mM tris, 30 mM NaCl, 80 mM L-Arg HCl, 5% w/v sucrose, 3.3% w/v mannitol, 0.01% w/v P188, pH 7.3 and formulations F8 to F10 with varying types and concentrations of salts. FIG. 9B shows post-lyophilization genome titer recovery assessed by comparison of viral genome titers in the pre-lyophilization formulations and the reconstituted post-lyophilization products.

FIG. 10A shows particle size analysis by DLS, FIG. 10B shows viral genome titer analysis by ddPCR, and FIG. 10C shows analysis of capsid purity by percentage of full capsid using AEC-UPLC.

FIG. 11A shows particle size analysis by DLS, FIG. 11B shows viral genome titer analysis by ddPCR, and FIG. 11C shows analysis of capsid purity by percentage of full capsid using AEX-UPLC.

DETAILED DESCRIPTION

Figure 1B:
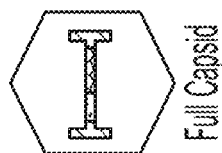
FIGS. 1A and 1B illustrate an AAV capsid comprising a heterologous nucleic acid molecule (e.g., a therapeutic gene or gene of interest (GOI)) (FIG. 1A); and empty, partially-full and full capsids (FIG. 1B).
Figure 1B:
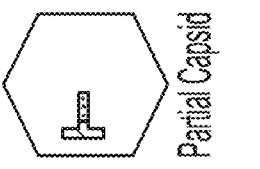
Figure 1B:
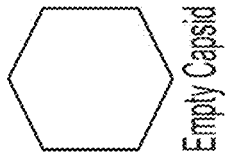
Figure 1A:
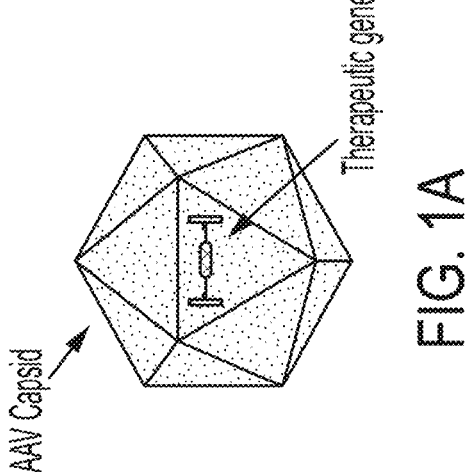

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "include," "includes," and "including," are meant to be non-limiting and are understood to mean "comprise," "comprises," and "comprising," respectively. As used herein, the term "and/or" refers to and encompasses any and all possible combinations of one or more of the associated listed items, as well as the lack of combinations when interpreted in the alternative ("or"). As used herein, the term "or" refers to any one member of a particular list and also includes any combination of members of that list. As used herein, the terms "a" and "an" and "the"

and similar referents in the context of describing the disclosure (especially in the context of the following claims) are to be construed to cover both the singular and the plural, unless otherwise indicated herein or clearly contradicted by context.

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

"Adeno-associated virus" or "AAV" is a non-pathogenic parvovirus, with single-stranded DNA, a genome of approximately 4.7 kb, not enveloped and has icosahedric conformation. AAV was first discovered in 1965 as a contaminant of adenovirus preparations. AAV belongs to the Dependovirus genus and Parvoviridae family, requiring helper functions from either herpes virus or adenovirus for replication. In the absence of helper virus, AAV can set up latency by integrating into human chromosome 19 at the 19q13.4 location. The AAV genome consists of two open reading frames (ORF), one for each of two AAV genes, Rep and Cap. The AAV DNA ends have a 145-bp inverted terminal repeat (ITR), and the 125 terminal bases are palindromic, leading to a characteristic T-shaped hairpin structure.

A "recombinant viral particle" refers to a viral particle including one or more heterologous sequences (e.g., a nucleic acid sequence not viral origin) that may be flanked by at least one viral nucleotide sequence.

A "recombinant AAV particle" refers to a adeno-associated viral particle including one or more heterologous sequences (e.g., nucleic acid sequence not of AAV origin) that may be flanked by at least one, for example, two, AAV inverted terminal repeat sequences (ITRs). Such rAAV particles can be replicated and packaged when present in a host cell that has been infected with a suitable helper virus (or that is expressing suitable helper functions) and that is expressing AAV rep and cap gene products (i.e., AAV Rep and Cap proteins).

A "viral particle" refers to a viral particle composed of at least one viral capsid protein and an encapsulated viral genome.

"Heterologous" means derived from a genotypically distinct entity from that of the rest of the entity to which it is compared or into which it is introduced or incorporated. For example, a nucleic acid introduced by genetic engineering techniques into a different cell type is a heterologous nucleic acid (and, when expressed, can encode a heterologous polypeptide). Similarly, a cellular sequence (e.g., a gene or portion thereof) that is incorporated into a viral particle is a heterologous nucleotide sequence with respect to the viral particle.

The terms "empty viral capsids" or "empty capsids" refer to capsids not containing a heterologous nucleic acid molecule (e.g., a therapeutic gene), as illustrated in FIG. 1B.

The terms "partially-full viral capsids" or "partially full capsids" refer to capsids containing only a portion of a heterologous nucleic acid molecule (e.g., a therapeutic gene), as illustrated in FIG. 1B.

The terms "full viral capsids" or "full capsids" refer to capsids containing a complete heterologous nucleic acid molecule (e.g., a therapeutic gene or gene of interest), as illustrated in FIG. 1B.

The term "pharmaceutically acceptable," as used in connection with compositions described herein, refers to molecular entities and other ingredients of such compositions that are physiologically tolerable and do not typically produce untoward reactions when administered to a subject. Preferably, the term "pharmaceutically acceptable" means approved by a regulatory agency of the Federal or a state government or listed in the U.S. Pharmacopeia or other generally recognized pharmacopeia for use in mammals, and more particularly in humans. A "pharmaceutically acceptable salt" is a salt that can be formulated into a compound or conjugate for pharmaceutical use including, e.g., metal salts (sodium, potassium, magnesium, calcium, etc.) and salts of ammonia or organic amines that is safe for administration to a subject (e.g., a human) in a drug formulation.

As used herein, a "physiological concentration" of salt refers to a salt concentration of between about 100 mM and about 200 mM of a pharmaceutically acceptable salt.

As used herein, a "sub-physiological concentration" of salt refers to a salt concentration of less than about 100 mM of a pharmaceutically acceptable salt. In certain embodiments, a sub-physiological concentration of salt is less than about 80 mM of a pharmaceutically acceptable salt. In another embodiment, a sub-physiological concentration of salt is less than about 70 mM, less than about 60 mM, less than about 50 mM, less than about 40 mM, less than about 30 mM, less than about 20 mM, or less than about 10 mM of a pharmaceutically acceptable salt.

As used herein, the terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or slowing the development/progression of the disease or a relapse thereof or at least one clinical or sub-clinical symptom thereof; or (3) relieving the disease, i.e., causing regression of the state, disorder or condition or at least one of its clinical or sub-clinical symptoms. As used these terms, do not necessarily imply 100% or complete treatment. Rather, there are varying degrees of treatment of which one of ordinary skill in the art recognizes as having a potential benefit or therapeutic effect. The benefit to a subject to be treated is either statistically significant or at least perceptible to the patient or to the physician.

As used herein, a "therapeutically effective amount or dose" or "sufficient amount or dose" refers to a dose that produces effects for which it is administered. The exact dose will depend on the purpose of the treatment, and will be ascertainable by one skilled in the art using known techniques.

The terms "patient" and "subject" are used interchangeably and are used in their conventional sense to refer to a living organism suffering from or prone to a condition that can be prevented or treated by administration of a composition of the present disclosure, and includes both humans and non-human animals. Examples of subjects include, but are not limited to, humans, chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, adult, juvenile and newborn individuals are contemplated.

As used herein, "storage" means that a formulation is not immediately administered to a subject once prepared, but is kept for a period of time under particular conditions (e.g., particular temperature, etc.) prior to use. For example, a liquid or lyophilized formulation can be kept for days, weeks, months or years, prior to administration to a subject under varied temperatures such as refrigerated (e.g., 0° to 10° C.) or room temperature (e.g., temperature up to 32° C.).

In preferred embodiments, the formulations and compositions of the present disclosure are sterile. By "sterile" is meant that there are substantially no immunogenic components in the composition, such as for example substantially no microbes (e.g., fungi, bacteria, non-AAV viruses, spore forms, and the like).

GENERAL DESCRIPTION

The present disclosure provides formulations, e.g., pharmaceutical formulations and lyophilized compositions, compatible for administration to a subject (e.g., upon reconstitution), and which are also suitable for long-term storage of AAV while maintaining stability and minimizing loss of AAV potency. In certain embodiments, the pharmaceutical formulations and compositions provided herein retain significant AAV activity when stored for extended periods of time. In certain embodiments, the pharmaceutical formulations and compositions discussed herein reduce or retard degradation and/or aggregation.

A particular challenge for AAV formulation and product development is that long-term storage of AAV products is often not efficient, resulting in shorter shelf-life (typically 12 to 18 months) compared to recombinant protein-based biologics. For example, formulations for existing AAV products (Luxturna® and Zolgensma®) only support limited shelf-life of 12 months at −60° C., and only 14 days of stability for Zolgensma® at 2-8° C. Frozen AAV products also present practical challenges for supply chain and inventory management, especially when low temperatures (e.g., below −65° C.) are required for shipping, distribution, and storage.

Lyophilized compositions, such as those discussed herein, address the challenges of both storage and supply chain management. In particular, the formulations and compositions of the present disclosure utilize carefully chosen excipients and concentrations to assure long-term storage stability in the solid state to support shelf-life, and room temperature stability in the liquid state (e.g., for typically a minimum of 48 hours) to support manufacturing operations and the conditions for clinical/therapeutic applications. Moreover, the lyophilized compositions of the present disclosure provide cake elegance and acceptable reconstitution properties.

The lyophilization cycle discussed herein includes four stages: freezing, annealing (in the presence of bulking agents such as mannitol or glycine), primary drying, and secondary drying. The pharmaceutical formulation subjected to lyophilization plays an important role in determining the quality of the drug product as the freezing followed by drying processes can impose a variety of stresses such as cold denaturation, solute (protein) concentration (increases caused by freezing concentrate), formation of ice crystals, crystallization of important excipients (e.g., buffers, salts), and pH changes. These stresses can induce protein conformational changes and ultimately impact the stability of the lyophilized drug product if not carefully considered in the selection of formulation excipients.

There are several challenges for a lyophilized AAV product that must be addressed during formulation development. First, AAV formulations require use of high ionic strength in order to prevent aggregation, but salts can greatly reduce the collapse temperature (Tc) or the glass transition temperature (Tg') for the amorphous systems, which may require use of lower freezing temperature during the freezing step, and consequently lead to an insufficient sublimation process. Second, AAV drug products are typically formulated with low concentrations in the range of 1E12 to 1E13 vector genome copy (vg)/mL, corresponding to approximately 0.01-0.2 mg/mL, leading to further reduced Tg' and posing risks of losing AAV due to adsorption on different surfaces. Third, due to the low concentration of AAV, it may be necessary to include a bulking agent in the formulation to prevent AAV from being lost from the vial during drying and to maintain structural integrity of the cake from collapse, but in doing so the bulking agent may not achieve sufficient crystallization during the annealing step and may continue to crystalize during secondary drying and subsequent storage in the dried solid, which may in turn affect reconstitution as well as the stability of the lyophilized drug product.

These and other challenges are addressed by the pharmaceutical formulations and compositions of the present disclosure. In certain embodiments, the present disclosure provides formulations of AAV comprising a therapeutically effective amount or dose of an AAV, one or more buffering agents providing a suitable pH to the formulation, one or more pharmaceutically acceptable salts, a stabilizing concentration of one or more sugars and/or sugar alcohols, a non-ionic surfactant, and a bulking agent. Generally, the AAV formulations provided herein are suitable for pharmaceutical administration.

Adeno-Associated Viral Particles

The AAV particles may be recombinant AAV (rAAV) particles. The rAAV particle includes an AAV vector encoding a heterologous transgene or heterologous nucleic acid molecule. The AAV particles may be avian AAV, bovine AAV, canine AAV, equine AAV, ovine AAV, primate AAV, and non-primate AAV.

In some aspects, the AAV particle contains a heterologous nucleic acid molecule (e.g., a therapeutic gene or gene of interest). In some aspects, the heterologous nucleic acid molecule is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit.beta.-globin promoter and the elongation factor 1-alpha promoter (EF1-alpha) promoter. In some aspects, the promoter comprises a human beta-glucuronidase promoter or a cytomegalovirus enhancer linked to a chicken beta-actin (CBA) promoter. The promoter can be a constitutive, inducible or repressible promoter. In some aspects, the present disclosure provides a recombinant vector comprising a nucleic acid encoding a heterologous transgene of the present disclosure operably linked to a CBA promoter. In some cases, the native promoter, or fragment thereof, for the transgene will be used. The native promoter can be used when it is desired that expression of the transgene should mimic the native expression. The native promoter may be used when expression of the transgene must be regulated temporally or developmentally, or in a tissue-specific manner, or in response to specific transcriptional stimuli. In a further aspect, other native expression control elements, such as enhancer elements, polyadenylation sites or Kozak consensus sequences may also be used to mimic the native expression.

In exemplary embodiments, the pharmaceutical formulations and compositions of the present disclosure comprises AAV. The AAV may be of any AAV serotype. In exemplary aspects, the AAV is of AAV1 serotype, AAV2 serotype, AAV3 serotype, AAV4 serotype, AAV5 serotype, AAV6 serotype, AAV7 serotype, AAV8 serotype, AAV9 serotype, or AAV10 serotype. In exemplary aspects, the AAV is of AAV1 serotype. In exemplary aspects, the AAV is of AAV5 serotype. In exemplary aspects, the AAV is of AAV8 serotype. In exemplary aspects, the AAV is of AAV9 serotype. In some, cases, the AAV is AAV11, AAV12, AAV-DJ, AAV-DJ/8, AAV-Rh10, AAV-retro, AAV-PHP.B, AAV8-PHP.eB, or AAV-PHP.S. In some embodiments, the AAV particles are of serotype AAV1, AAV5, AAV8, or AAV9.

In exemplary aspects, the pharmaceutical formulations and compositions comprise a high titer AAV product. In exemplary aspects, the pharmaceutical formulations and compositions comprise at least about 10E10 virus particles (vp) or at least about 10E11 virus particles (vp) or at least about 10E12 virus particles (vp) or at least about 10E13 virus particles (vp). In exemplary aspects, the pharmaceutical formulations and compositions comprise at least about 10E14 virus particles (vp) or at least about 10E15 virus particles (vp), e.g., at least about 2×10E15 virus particles (vp), or at least about 5×10E15 virus particles (vp). The pharmaceutical formulations and compositions comprise also about 10E10 vector genomes or viral genomes (vg) or at least about 10E11 vector or viral genomes (vg) or at least about 10E12 vector genomes or viral genomes (vg) or at least about 10E13 vector genomes or viral genomes (vg). In exemplary aspects, the pharmaceutical formulations and compositions comprises at least about 10E14 vector genomes or viral genomes (vg) or at least about 10E15 vector genomes or viral genomes (vg), e.g., at least about 2×10E15 vector genomes or viral genomes (vg), or at least about 5×10E15 vector genomes or viral genomes (vg).

Excipients and pH

The pharmaceutical formulations and compositions (which include liquid pharmaceutical formulations, lyophilized pharmaceutical compositions, and reconstituted drug products, unless otherwise specifically indicated) of the present disclosure include carefully selected excipients at concentrations to maintain stability of the AAV particles during manufacturing and use, as well as over long-term storage under conditions that ease supply chain logistics. In various embodiments, the present disclosure includes liquid pharmaceutical formulations, lyophilized pharmaceutical compositions, and reconstituted drug products containing AAV particles (e.g., as discussed above or herein) in combination with one or more buffers within a defined pH range, one or more salts, one or more sugars or sugar alcohols, one or more bulking agents, and one or more surfactants. The concentrations discussed in connection with the various excipients below or herein refer to the liquid pharmaceutical formulations, such formulations that are subsequently subjected to lyophilization, or to reconstituted compositions prepared by reconstitution of the lyophilized compositions. The various excipients included in the compositions of the present disclosure include salts, sugars and bulking agent, among others. Salts can contribute to stabilization of the AAV particles by mitigating the formation of aggregates, but can also greatly reduce the collapse temperature. Sugars can act as a cryo-protectant during freeze drying, but can also inhibit crystallization of the bulking agent. Failure to sufficiently crystallize the bulking agent will deleteriously affect the glass transition temperature and compromise storage stability. Thus, careful selection of excipients and concentrations is necessary to produce a stable AAV formulation and lyophilized composition.

A. Buffers and pH

The liquid pharmaceutical formulations, lyophilized pharmaceutical compositions, and reconstituted drug products of the present disclosure include pharmaceutically acceptable buffering agents. In some cases, the buffering agents include, without limitation, phosphate buffers, histidine buffers, sodium citrate buffers, HEPES buffers, Tris buffers, Bicine buffers, glycine buffers, N-glycylglycine buffers, sodium acetate buffers, sodium carbonate buffers, glycyl glycine buffers, lysine buffers, arginine buffers, sodium phosphate buffers, and/or mixtures thereof. In some embodiments, the buffering agent is a phosphate buffer (e.g., a sodium phosphate buffer). In some embodiments, the buffering agent is a Tris buffer.

In exemplary embodiments, the pharmaceutical compositions of the present disclosure comprises about 1 to about 30, about 1 mM to about 20 mM, about 5 mM to about 25 mM, about 5 to about 15, about 7 mM to about 13 mM, or about 8 mM to about 12 mM of a buffering agent. In exemplary aspects, the pharmaceutical composition comprises about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, or about 25 mM of a buffering agent.

In exemplary embodiments, the pharmaceutical compositions of the present disclosure comprises about 1 mM to about 20 mM, about 5 mM to about 15 mM, about 8 mM to about 12 mM, or 10 mM±1 mM Tris buffer. In exemplary embodiments, the pharmaceutical compositions of the present disclosure comprises about 1 mM to about 20 mM, about 5 mM to about 15 mM, about 8 mM to about 12 mM, or 10 mM±1 mM sodium phosphate buffer. In various embodiments, the pharmaceutical compositions comprise about 5 mM, about 6 mM, about 7 mM, about 8 mM, about 9 mM, about 10 mM, about 11 mM, about 12 mM, about 13 mM, about 14 mM, or about 15 mM Tris buffer. In various embodiments, the pharmaceutical compositions comprise about 5 mM, about 6 mM, about 7 mM, about 8 mM, about 9 mM, about 10 mM, about 11 mM, about 12 mM, about 13 mM, about 14 mM, or about 15 mM sodium phosphate buffer. In certain embodiments, the pharmaceutical compositions comprise 10 mM±2 mM Tris buffer. In certain embodiments, the pharmaceutical compositions comprise 10 mM±2 mM sodium phosphate buffer.

In exemplary embodiments, the pharmaceutical compositions of the present disclosure has a physiologically compatible pH. In certain embodiments, the AAV formulations are provided that contain a buffering agent suitable to maintain the formulation at or near a neutral pH.

In exemplary embodiments, the pH of the pharmaceutical compositions is about 6.5 to about 9.0, about 6.5 to about 8.0, about 6.9 to about 7.7, or about 7.0 to about 7.5. In certain embodiments, the pH of the formulation is about 6.5 or about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In exemplary embodiments, the pH of the pharmaceutical compositions is about 7.2, about 7.3, or about 7.4. In certain embodiments, the pH of the pharmaceutical composition is 7.3±0.1. In certain embodiments, the pH of the pharmaceutical composition is 7.3±0.05.

B. Salts

The liquid pharmaceutical formulations, lyophilized pharmaceutical compositions, and reconstituted drug products of the present disclosure include one or more pharmaceutically acceptable salts.

In various embodiments, the pharmaceutically acceptable salts include, but are not limited to, metal salts such as sodium, potassium and cesium salts; alkaline earth metal salts such as calcium and magnesium salts; organic amine salts such as triethylamine, guanidine and N-substituted guanidine salts, acetamidine and N-substituted acetamidine, pyridine, picoline, ethanolamine, triethanolamine, dicyclohexylamine, and N,N'-dibenzylethylenediamine salts. Pharmaceutically acceptable salts (of basic nitrogen centers) include, but are not limited to inorganic acid salts such as the hydrochloride, hydrobromide, sulfate, phosphate; organic acid salts such as trifluoroacetate and maleate salts; sulfonates such as methanesulfonate, ethanesulfonate, benzenesulfonate, p-toluenesulfonate, camphor sulfonate and naphthalenesulfonate; amino acid salts such as arginate, alaninate, asparaginate and glutamate; and carbohydrate salts such as gluconate and galacturonate. Non-limiting examples of pharmaceutically acceptable salts include, without limitation, sodium salts, ammonium salts, potassium salts, calcium salts, and magnesium salts (e.g., sodium, ammonium, potassium, calcium, and magnesium chloride; sodium, ammonium, potassium, calcium and magnesium acetate; sodium, ammonium, potassium, calcium and magnesium citrate; sodium, ammonium, potassium, calcium and magnesium phosphate; sodium, ammonium, potassium, calcium and magnesium fluoride; sodium, ammonium, potassium, calcium and magnesium bromide; and sodium, ammonium, potassium, calcium and magnesium iodide). In some case, the pharmaceutically acceptable salt is sodium chloride. In some cases, the pharmaceutically acceptable salt is arginine hydrochloride (L-arginine hydrochloride).

In exemplary embodiments, the pharmaceutical compositions of the present disclosure comprise about 0 mM to about 150 mM, about 5 mM to about 150 mM, about 5 mM to about 100 mM, about 5 mM to about 90 mM, about 5 mM to about 80 mM, about 5 mM to about 70 mM, about 5 mM to about 60 mM, about 5 mM to about 50 mM, about 5 mM to about 40 mM, 5 mM to about 30 mM, about 10 mM to about 50 mM, about 15 mM to about 45 mM, about 20 mM to about 40 mM, about 25 mM to about 35 mM, about 30 mM to about 130 mM, about 40 mM to about 120 mM, about 50 mM to about 110 mM, about 60 mM to about 100 mM, about 70 mM to about 90 mM, or about 75 mM to about 85 mM of a pharmaceutically acceptable salt (as defined above; e.g., a first salt, a second salt, or both a first and second salt). In exemplary embodiments, the pharmaceutical compositions comprise about 0 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, or about 150 mM of a pharmaceutically acceptable salt (e.g., a first salt, a second salt, or both a first and second salt). In some embodiments, the pharmaceutical compositions comprise about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, about 50 mM, about 51 mM, about 52 mM, about 53 mM, about 54 mM, about 55 mM, about 56 mM, about 57 mM, about 58 mM, about 59 mM, about 60 mM, about 61 mM, about 62 mM, about 63 mM, about 64 mM, about 65 mM, about 66 mM, about 67 mM, about 68 mM, about 69 mM, about 70 mM, about 71 mM, about 72 mM, about 73 mM, about 74 mM, about 75 mM, about 76 mM, about 77 mM, about 78 mM, about 79 mM, about 80 mM, about 81 mM, about 82 mM, about 83 mM, about 84 mM, about 85 mM, about 86 mM, about 87 mM, about 88 mM, about 89 mM, about 90 mM, about 91 mM, about 92 mM, about 93 mM, about 94 mM, about 95 mM, about 96 mM, about 97 mM, about 98 mM, about 99 mM, about 100 mM, about 101 mM, about 102 mM, about 103 mM, about 104 mM, or about 105 mM of a pharmaceutically acceptable salt (e.g., a first salt, a second salt, or both a first and second salt).

In certain embodiments, the pharmaceutical compositions of the present disclosure comprise about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, or about 50 mM of sodium chloride. In some embodiments, the compositions comprise 30 mM±5 mM sodium chloride. In some embodiments, the compositions comprise 30 mM±3 mM sodium chloride. In some embodiments, the compositions comprise 30 mM±1 mM sodium chloride. In certain embodiments, the pharmaceutical compositions of the present disclosure comprise about 60 mM, about 61 mM, about 62 mM, about 63 mM, about 64 mM, about 65 mM, about 66 mM, about 67 mM, about 68 mM, about 69 mM, about 70 mM, about 71 mM, about 72 mM, about 73 mM, about 74 mM, about 75 mM, about 76 mM, about 77 mM, about 78 mM, about 79 mM, about 80 mM, about 81 mM, about 82 mM, about 83 mM, about 84 mM, about 85 mM, about 86 mM, about 87 mM, about 88 mM, about 89 mM, about 90 mM, about 91 mM, about 92 mM, about 93 mM, about 94 mM, about 95 mM, about 96 mM, about 97 mM, about 98 mM, about 99 mM, or about 100 mM of arginine hydrochloride. In some embodiments, the compositions comprise 80 mM±10 mM arginine hydrochloride. In some embodiments, the compositions comprise 80 mM±5 mM arginine hydrochloride. In some embodiments, the compositions comprise 80 mM±3 mM arginine hydrochloride.

C. Surfactants

The liquid pharmaceutical formulations, lyophilized pharmaceutical compositions, and reconstituted drug products of the present disclosure include one or more surfactants.

Non-ionic surfactants, as discussed herein, substantially reduce the loss of AAV on surfaces and prevent formation of visible particles of the pharmaceutical compositions of the present disclosure. Accordingly, in certain embodiments, pharmaceutical compositions contain a stabilizing concentration of a non-ionic surfactant. Pharmaceutically acceptable non-ionic surfactants that may be used in the compositions discussed herein include, without limitation, polysorbate 80 (Tween 80; PS80), polysorbate 20 (Tween 20; PS20), and various poloxamers (e.g., poloxamer 188), or mixtures thereof. In some cases, specific non-ionic surfactants that can be included in the formulations and compositions of the present disclosure include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 181, poloxamer 188, poloxamer 407; or polyethylene glycol (PEG). In some embodiments, the non-ionic surfactant used in the compositions is polysorbate 80. In some embodiments, the non-ionic surfactant used in the compositions is poloxamer 188.

In certain embodiments, the pharmaceutical compositions of the present disclosure comprise from about 0.001% (w/v) to about 0.1% (w/v) non-ionic surfactant. In various embodiments, the compositions comprise about 0.001% (w/v), about 0.0015% (w/v), about 0.002% (w/v), about 0.0025% (w/v), about 0.003% (w/v), about 0.0035% (w/v), about 0.004% (w/v), about 0.0045% (w/v), about 0.005% (w/v), about 0.0055% (w/v), about 0.006% (w/v), about 0.0065% (w/v), about 0.007% (w/v), about 0.0075% (w/v), about 0.008% (w/v), about 0.0085% (w/v), about 0.009% (w/v), about 0.0095% (w/v), or about 0.01% (w/v) non-ionic surfactant. In various embodiments, the compositions comprise about 0.01% (w/v), about 0.015% (w/v), about 0.02% (w/v), about 0.025% (w/v), about 0.03% (w/v), about 0.035% (w/v), about 0.04% (w/v), about 0.045% (w/v), about 0.05% (w/v), about 0.055% (w/v), about 0.06% (w/v), about 0.065% (w/v), about 0.07% (w/v), about 0.075% (w/v), about 0.08% (w/v), about 0.085% (w/v), about 0.09% (w/v), about 0.095% (w/v), or about 0.1% (w/v) non-ionic surfactant. In certain embodiments, the pharmaceutical compositions of the present disclosure comprise 0.005% w/v±0.001% w/v non-ionic surfactant.

In some exemplary embodiments, the pharmaceutical compositions of the present disclosure comprise about 0.001% (w/v) to about 0.01% (w/v) polysorbate 80. In some exemplary embodiments, the pharmaceutical compositions of the present disclosure comprise about 0.001% (w/v) to about 0.01% (w/v) poloxamer 188. In some embodiments, the pharmaceutical compositions comprise about 0.001% (w/v), about 0.0015% (w/v), about 0.002% (w/v), about 0.0025% (w/v), about 0.003% (w/v), about 0.0035% (w/v), about 0.004% (w/v), about 0.0045% (w/v), about 0.005% (w/v), about 0.0055% (w/v), about 0.006% (w/v), about 0.007% (w/v), about 0.0075% (w/v), about 0.008% (w/v), about 0.0085% (w/v), about 0.009% (w/v), about 0.0095% (w/v), or about 0.01% (w/v) polysorbate 80. In some embodiments, the pharmaceutical compositions comprise about 0.001% (w/v), about 0.0015% (w/v), about 0.002% (w/v), about 0.0025% (w/v), about 0.003% (w/v), about 0.0035% (w/v), about 0.004% (w/v), about 0.0045% (w/v), about 0.005% (w/v), about 0.0055% (w/v), about 0.006% (w/v), about 0.0065% (w/v), about 0.007%

(w/v), about 0.0075% (w/v), about 0.008% (w/v), about 0.0085% (w/v), about 0.009% (w/v), about 0.0095% (w/v), or about 0.01% (w/v) poloxamer 188. In certain embodiments, the pharmaceutical compositions of the present disclosure comprise about 0.005% w/v±0.001% w/v polysorbate 80. In certain embodiments, the pharmaceutical compositions of the present disclosure comprise about 0.005% w/v±0.001% w/v poloxamer 188.

D. Sugars

The liquid pharmaceutical formulations, lyophilized pharmaceutical compositions, and reconstituted drug products of the present disclosure include one or more sugars.

Inclusion of one of more sugars (e.g., at between about 1% to about 20%) improves the stability of the liquid and/or lyophilized formulations of the present disclosure. For example, the sugar allows for better properties during freeze/thawing cycles. Accordingly, in certain embodiments, the pharmaceutical compositions of the present disclosure contain from about 1% to about 10% of one or more sugars. Any sugar such as mono-, di-, or polysaccharides, or water-soluble glucans, including for example fructose, glucose, mannose, sorbose, xylose, maltose, lactose, sucrose, dextran, trehalose, pullulan, dextrin, cyclodextrin, soluble starch, hydroxyethyl starch, and carboxymethylcellulose may be used in various embodiments. In some embodiments, the sugar is sucrose, trehalose, or a combination thereof. In certain embodiments, the trehalose is trehalose dihydrate. In some embodiments, the sugar is sucrose. In some embodiments, the sugar is trehalose.

The sugars may be used individually or in combination. In some embodiments, the sugar, or combination thereof, is present in the formulation or composition at a concentration of about 1% to about 10% (w/v), about 2% (w/v) to about 8% (w/v), about 2.5% to about 7.5% (w/v), about 3% (w/v) to about 7% (w/v), or about 4% to about 6% (w/v). In some embodiments, the pharmaceutical compositions of the present disclosure comprise about 1.0% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2.0% (w/v), about 2.1% (w/v), about 2.2% (w/v), about 2.3% (w/v), about 2.4% (w/v), about 2.5% (w/v), about 2.6% (w/v), about 2.7% (w/v), about 2.8% (w/v), about 2.9% (w/v), about 3.0% (w/v), about 3.1% (w/v), about 3.2% (w/v), about 3.3% (w/v), about 3.4% (w/v), about 3.5% (w/v), about 3.6% (w/v), about 3.7% (w/v), about 3.8% (w/v), about 3.9% (w/v), about 4.0% (w/v), about 4.1% (w/v), about 4.2% (w/v), about 4.3% (w/v), about 4.4% (w/v), about 4.5% (w/v), about 4.6% (w/v), about 4.7% (w/v), about 4.8% (w/v), about 4.9% (w/v), about 5.0% (w/v), about 5.1% (w/v), about 5.2% (w/v), about 5.3% (w/v), about 5.4% (w/v), about 5.5% (w/v), about 5.6% (w/v), about 5.7% (w/v), about 5.8% (w/v), about 5.9% (w/v), about 6.0% (w/v), about 6.1% (w/v), about 6.2% (w/v), about 6.3% (w/v), about 6.4% (w/v), about 6.5% (w/v), about 6.6% (w/v), about 6.7% (w/v), about 6.8% (w/v), about 6.9% (w/v), about 7.0% (w/v), about 7.1% (w/v), about 7.2% (w/v), about 7.3% (w/v), about 7.4% (w/v), about 7.5% (w/v), about 7.6% (w/v), about 7.7% (w/v), about 7.8% (w/v), about 7.9% (w/v), about 8.0% (w/v), about 8.1% (w/v), about 8.2% (w/v), about 8.3% (w/v), about 8.4% (w/v), about 8.5% (w/v), about 8.6% (w/v), about 8.7% (w/v), about 8.8% (w/v), about 8.9% (w/v), about 9.0% (w/v), about 9.1% (w/v), about 9.2% (w/v), about 9.3% (w/v), about 9.4% (w/v), about 9.5% (w/v), about 9.6% (w/v), about 9.7% (w/v), about 9.8% (w/v), about 19.9% (w/v), or about 10% (w/v) sugar.

In various embodiments, the compositions of the present disclosure include about 2.5% w/v to about 7.5% w/v sucrose. In some embodiments, the compositions contain 4% w/v to 6% w/v sucrose. In some embodiments, the compositions contain 5% w/v±0.5% w/v sucrose. In various embodiments, the compositions of the present disclosure include about 2.5% w/v to about 7.5% w/v trehalose. In some embodiments, the compositions contain 4% w/v to 6% w/v trehalose. In some embodiments, the compositions contain 5% w/v±0.5% w/v trehalose.

E. Bulking Agents

The liquid pharmaceutical formulations, lyophilized pharmaceutical compositions, and reconstituted drug products of the present disclosure include one or more bulking agents.

Inclusion of one of more sugars (e.g., at between about 1c/o to about 10%) improves the stability of the liquid and/or lyophilized formulations of the present disclosure. For example, the bulking agent as discussed herein allows for production of a better lyophilized composition with improved stability and reconstitution properties. Accordingly, in certain embodiments, the pharmaceutical compositions of the present disclosure contain from about 1% to about 10% of one or more bulking agents. In various embodiments, the bulking agent included in the pharmaceutical compositions of the present disclosure may include, without limitation, mannitol, glycine, polymers such as dextran, polyvinylpyrolidone, carboxymethylcellulose, lactose, sorbitol, or xylitol In some embodiments, the bulking agent is mannitol. In some embodiments, the bulking agent is glycine.

The bulking agents may be used individually or in combination. In some embodiments, the bulking agent, or combination thereof, is present in the formulation or composition at a concentration of about 1% to about 10% (w/v), about 1% (w/v) to about 6% (w/v), about 2% to about 4% (w/v), or about 3% (w/v) to about 3.5% (w/v). In some embodiments, the pharmaceutical compositions of the present disclosure comprise about 1.0% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2.0% (w/v), about 2.1% (w/v), about 2.2% (w/v), about 2.3% (w/v), about 2.4% (w/v), about 2.5% (w/v), about 2.6% (w/v), about 2.7% (w/v), about 2.8% (w/v), about 2.9% (w/v), about 3.0% (w/v), about 3.1% (w/v), about 3.2% (w/v), about 3.3% (w/v), about 3.4% (w/v), about 3.5% (w/v), about 3.6% (w/v), about 3.7% (w/v), about 3.8% (w/v), about 3.9% (w/v), about 4.0% (w/v), about 4.1% (w/v), about 4.2% (w/v), about 4.3% (w/v), about 4.4% (w/v), about 4.5% (w/v), about 4.6% (w/v), about 4.7% (w/v), about 4.8% (w/v), about 4.9% (w/v), about 5.0% (w/v), about 5.1% (w/v), about 5.2% (w/v), about 5.3% (w/v), about 5.4% (w/v), about 5.5% (w/v), about 5.6% (w/v), about 5.7% (w/v), about 5.8% (w/v), about 5.9% (w/v), about 6.0% (w/v), about 6.1% (w/v), about 6.2% (w/v), about 6.3% (w/v), about 6.4% (w/v), about 6.5% (w/v), about 6.6% (w/v), about 6.7% (w/v), about 6.8% (w/v), about 6.9% (w/v), about 7.0% (w/v), about 7.1% (w/v), about 7.2% (w/v), about 7.3% (w/v), about 7.4% (w/v), about 7.5% (w/v), about 7.6% (w/v), about 7.7% (w/v), about 7.8% (w/v), about 7.9% (w/v), about 8.0% (w/v), about 8.1% (w/v), about 8.2% (w/v), about 8.3% (w/v), about 8.4% (w/v), about 8.5% (w/v), about 8.6% (w/v), about 8.7% (w/v), about 8.8% (w/v), about 8.9% (w/v), about 9.0% (w/v), about 9.1% (w/v), about 9.2% (w/v), about 9.3% (w/v), about 9.4% (w/v), about 9.5% (w/v), about 9.6% (w/v), about 9.7% (w/v), about 9.8% (w/v), about 19.9% (w/v), or about 10% (w/v) bulking agent.

In various embodiments, the compositions of the present disclosure include about 2% w/v to about 4.5% w/v mannitol. In some embodiments, the compositions contain 3% w/v to 3.5% w/v mannitol. In some embodiments, the compositions contain 3.3% w/v±0.1% w/v mannitol. In various embodiments, the compositions of the present disclosure include about 2% w/v to about 4.5% w/v glycine. In some embodiments, the compositions contain 3% w/v to 3.5% w/v glycine. In some embodiments, the compositions contain 3.3% w/v±0.1% w/v glycine.

F. Ratios of Excipients

In various embodiments, the liquid pharmaceutical formulations, lyophilized pharmaceutical compositions, and reconstituted drug products of the present disclosure include defined ratios of specific excipients to enhance stability of the compositions. In some embodiments, the compositions include specified ratios of bulking agent to sugar (bulking agent:sugar). In some embodiments, the compositions include specified ratios of two salts (first salt:second salt).

In some cases, the bulking agent:sugar ratio is from about 1:1 to 1:10. In various embodiments, the bulking agent:sugar ratio is about 1:1, about 1:2, about 1:3, about 1:4, about 1:5, about 1:6, about 1:7, about 1:8, about 1:9, about 1:10, about 2:3, about 2:5, about 2:7, about 2:9, about 3:4, about 3:5, about 3:7, about 3:8, about 3:10, about 4:5, about 4:7, about 4:9, about 5:6, about 5:7, about 5:8, about 5:9, about 6:7, about 7:8, about 7:9, about 7:10, or about 8:9. In some embodiments, the bulking agent:sugar ratio is about 3.1:5, about 3.2:5, about 3.3:5, about 3.4:5, or about 3.5:5. In some cases, the bulking agent:sugar ratio is 3.3:5. In some cases, the bulking agent is mannitol, and the sugar is sucrose, and the ratio is from about 1:1 to 1:10. In various embodiments, the mannitol:sucrose ratio is about 1:1, about 1:2, about 1:3, about 1:4, about 1:5, about 1:6, about 1:7, about 1:8, about 1:9, about 1:10, about 2:3, about 2:5, about 2:7, about 2:9, about 3:4, about 3:5, about 3:7, about 3:8, about 3:10, about 4:5, about 4:7, about 4:9, about 5:6, about 5:7, about 5:8, about 5:9, about 6:7, about 7:8, about 7:9, about 7:10, or about 8:9. In some embodiments, the mannitol:sucrose ratio is about 2.8:5, about 2.9:5, about 3.0:5, about 3.1:5, about 3.2:5, about 3.3:5, about 3.4:5, about 3.5:5, about 3.6:5, about 3.7:5, or about 3.8:5. In some cases, the mannitol: sucrose ratio is 3.3:5.

In some cases, the first salt:second salt ratio is from about 1:1 to 1:10. In various embodiments, the first salt:second salt ratio is about 1:1, about 1:2, about 1:3, about 1:4, about 1:5, about 1:6, about 1:7, about 1:8, about 1:9, about 1:10, about 2:3, about 2:5, about 2:7, about 2:9, about 3:4, about 3:5, about 3:7, about 3:8, about 3:10, about 4:5, about 4:7, about 4:9, about 5:6, about 5:7, about 5:8, about 5:9, about 6:7, about 7:8, about 7:9, about 7:10, or about 8:9. In some embodiments, the first salt:second salt ratio is about 2.5:8, about 2.6:8, about 2.7:8, about 2.8:8, about 2.9:8, about 3.0:8, about 3.1:8, about 3.2:8, about 3.3:8, about 3.4:8, or about 3.5:8. In some cases, the first salt:second salt ratio is 3:8. In some cases, the first salt is sodium chloride, and the second salt is L-arginine hydrochloride, and the ratio is from about 1:1 to 1:10. In various embodiments, the NaCl:L-arginine hydrochloride ratio is about 1:1, about 1:2, about 1:3, about 1:4, about 1:5, about 1:6, about 1:7, about 1:8, about 1:9, about 1:10, about 2:3, about 2:5, about 2:7, about 2:9, about 3:4, about 3:5, about 3:7, about 3:8, about 3:10, about 4:5, about 4:7, about 4:9, about 5:6, about 5:7, about 5:8, about 5:9, about 6:7, about 7:8, about 7:9, about 7:10, or about 8:9. In some embodiments, the NaCl:L-arginine hydrochloride ratio is about 2.5:8, about 2.6:8, about 2.7:8, about 2.8:8, about 2.9:8, about 3.0:8, about 3.1:8, about 3.2:8, about 3.3:8, about 3.4:8, or about 3.5:8. In some cases, the NaCl:L-arginine hydrochloride ratio is 3:8.

G. Additional Optional Components

The liquid pharmaceutical formulations, lyophilized pharmaceutical compositions, and reconstituted drug products of the present disclosure may also optionally include additional components. In exemplary embodiments, the formulations or pharmaceutical compositions comprise any one or a combination of the following: acidifying agents, additives, adsorbents, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, solubilizing agents, solvents, stabilizing agents, surface active agents, surfactants, suspending agents, sweetening agents, therapeutic agents, thickening agents, tonicity agents, viscosity-increasing agents, water-absorbing agents, water-miscible cosolvents, water softeners, or wetting agents.

Lyophilization and Compositions

Lyophilized compositions are prepared by lyophilization of the pharmaceutical formulations discussed above or herein. In various aspects, the present disclosure includes such lyophilized compositions, and methods of producing stable lyophilized pharmaceutical compositions. Embodiments of the methods of producing the lyophilized AAV compositions discussed herein may also include producing the aqueous formulation, which is subsequently lyophilized.

The lyophilization process, in general, comprises (i) freezing, (ii) annealing, (iii), primary drying, and (iv) secondary drying. In some cases, the freezing is performed at a temperature of −45° C.±5° C. for a period of 60 minutes±10 minutes. In some cases, the freezing is performed both before and after the annealing. In some cases, the annealing is performed at a temperature of −20° C.±5° C. for a period of 6 hours±30 minutes. In some cases, the primary drying is performed at a temperature of −26° C.±5° C. for a period of 50 hours±10 hours. In some cases, the secondary drying is performed at a temperature of 35° C.±5° C. for a period of from 5 to 20 hours, or a period of 15 hours±5 hours.

In one embodiment, rAAV samples are filled into glass vials and placed in a lyophilization chamber. Samples may be initially incubated at about 5° C. for about 60 minutes, cooled from about 5° C. to about −45° C. at a ramp rate of about 0.5° C./min followed by an isothermal hold for about 60 minutes. Annealing may be performed at about −20° C. for about 6 hours at a ramp rate of about 0.5° C./min, cooled back to about −45° C. at a ramp rate of about 0.5° C./min followed by a hold for about 60 minutes. Primary drying may be performed at about −26° C. under about 50 mTorr chamber pressure for about 50 hours, followed by secondary drying at about 35° C. under about 100 mTorr for about 10 hours or 15 hours with a ramp rate of about 0.3° C./min for both primary and secondary drying. At the end of the lyophilization cycle, samples may be backfilled with nitrogen gas at about 80% atmospheric pressure, and capped and sealed.

In one embodiment, rAAV samples are filled into glass vials and placed in a lyophilization chamber. Samples may be initially incubated at a temperature of from about 1° C. to about 10° C. for a period of from about 30 minutes to about 90 minutes, cooled from the incubation temperature to a freezing temperature of from about −30° C. to about −60° C. at a ramp rate of from about 0.1° C./min to about 1° C./min followed by an isothermal hold for a period of from about 30 minutes to about 90 minutes. Annealing may be performed at a temperature of from about −10° C. to about −30° C. for a period of from about 4 hours to about 8 hours at a ramp rate of from about 0.1° C./min to about 1° C./min, and the samples may then be cooled back to a temperature of from about −30° C. to about −60° C. at a ramp rate of from about 0.1° C./min to about 1° C./min followed by a hold for a period of from about 30 minutes to about 90 minutes. Primary drying may be performed at a temperature of from about −20° C. to about −30° C. under from about 40 mTorr to about 60 mTorr chamber pressure for a period of from about 40 hours to about 60 hours, followed by secondary drying at a temperature of from about 25° C. to about 45° C. under a pressure of from about 75 mTorr to about 125 mTorr for a period of from about 5 hours to about 20 hours with a ramp rate of from about 0.1° C./min to about 1° C./min for both primary and secondary drying. At the end of the lyophilization cycle, samples may be backfilled with nitrogen gas at about 70%-90% atmospheric pressure, and capped and sealed.

In some embodiments, the rAAV samples are initially incubated at a temperature of about 10° C., about 9° C., about 8° C., about 7° C., about 6° C., about 5° C., about 4° C., about 3° C., about 2° C., about 1° C., or about 0° C. This incubation may be held for a period of from about 10 minutes to about 120 minutes or longer. In some embodiments, the rAAV samples are initially incubated for a period of 10 minutes, 20 minutes, 30 minutes, 40 minutes, 50 minutes, 60 minutes, 70 minutes, 80 minutes, 90 minutes, 100 minutes, 110 minutes, or 120 minutes or longer.

During lyophilization, the temperature of the composition (e.g., rAAV samples) may be reduced, for example to a temperature below the freezing point of water in the composition. For example, the temperature of the composition may be reduced to 0° C. or less, or −5° C. or less, or −10° C. or less, or −15° C. or less, or −20° C. or less, or −25° C. or less, or −30° C. or less, or −35° C. or less, or −40° C. or less, or −45° C. or less, or −50° C. or less, or −55° C. or less, or −60° C. or less, or −65° C. or less, or −70° C. or less during freezing as part of the lyophilization process. In various embodiments, the rAAV samples are held at the freezing temperature (e.g., −45° C.) for a period of about 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, or longer.

In some embodiments, annealing is performed at a temperature of from about −10° C. to about −30° C. In some cases, annealing is performed at a temperature of about −10° C., about −11° C., about −12° C., about −13° C., about −14° C., about −15° C., about −16° C., about −17° C., about −18° C., about −19° C., about −20° C., about −21° C., about −22° C., about −23° C., about −24° C., about −25° C., about −26° C., about −27° C., about −28° C., about −29° C., or about −30° C. In various embodiments, the samples are maintained at the annealing temperature for a period of from about 3 hours to about 9 hours or longer. In some cases, the samples are maintained at the annealing temperature of a period of about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, or about 9 hours, or longer.

In some embodiments, additional freezing is performed after annealing. In various embodiments, this additional freezing may be performed at a temperature and for a duration as discussed above or herein. For example, the rAAV samples may be reduced to about −45° C. for a period of about 60 minutes.

Primary drying may be performed as part of the lyophilization process at a temperature of from about −10° C. to about −50° C., at a pressure of from about 1 mTorr to about 10 Torr, and for a period of from about 10 hours to about 200 hours or longer.

In some embodiments, primary drying is performed at a temperature of from about −20° C. to about −30° C. In various embodiments, primary drying is performed at a temperature of about −10° C., about −11° C., about −12° C., about −13° C., about −14° C., about −15° C., about −16° C., about −17° C., about −18° C., about −19° C., about −20° C., about −21° C., about −22° C., about −23° C., about −24° C., about −25° C., about −26° C., about −27° C., about −28° C., about −29° C., or about −30° C. In some cases, primary drying is performed at a temperature of about −25° C. In some cases, primary drying is performed at a temperature of about −26° C. In some cases, primary drying is performed at a temperature of about −27° C.

In some embodiments, the pressure surrounding the composition during primary drying is reduced below standard atmospheric pressure. For example, the pressure surrounding the composition may be reduced to 100 Torr or less, or 10 Torr or less, or 1 Torr or less, or 500 mTorr or less, or 400 mTorr or less, or 300 mTorr or less, or 200 mTorr or less, or 100 mTorr or less, or 90 mTorr or less, or 80 mTorr or less, or 70 mTorr or less, or 60 mTorr or less, or 50 mTorr or less, or 40 mTorr or less, or 30 mTorr or less, or 20 mTorr or less, or 10 mTorr or less, or 5 mTorr or less, or 1 mTorr or less. In some cases, the pressure surrounding the composition is reduced to from about 40 mTorr to about 60 mTorr or less. In some cases, the pressure surrounding the composition is reduced to from about 45 mTorr to about 55 mTorr or less. In some cases, pressure surrounding the composition is reduced to from about 50 mTorr.

In various embodiments, primary drying is performed for a period of from about 10 hours to about 200 hours or more. In some cases, primary drying is performed for a period of about 10 hours, about 15 hours, about 20 hours, about 25 hours, about 30 hours, about 35 hours, about 40 hours, about 45 hours, about 50 hours, about 55 hours, about 60 hours, about 65 hours, bout 70 hours, about 75 hours, about 80 hours, about 85 hours, about 90 hours, about 95 hours, about 100 hours, about 120 hours, about 140 hours, about 160 hours, about 180 hours, or about 200 hours or longer. In some cases, primary drying is performed for a period of from about 40 hours to about 60 hours. In some cases, primary drying is performed for a period of from about 45 hours to about 55 hours. In some cases, primary drying is performed for a period of from about 50 hours.

Secondary drying may be performed as part of the lyophilization process at a temperature of from about 5° C. to about 65° C., at a pressure of from about 1 mTorr to about 10 Torr, and for a period of from about 1 hour to about 30 hours or longer.

In some embodiments, secondary drying is performed at a temperature of from about 20° C. to about −50° C. In various embodiments, secondary drying is performed at a temperature of about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some cases, secondary drying is performed at a temperature of from about 30° C. to about 40° C. In some cases, secondary drying is performed at a temperature of about 35° C.

In some embodiments, the pressure surrounding the composition during secondary drying is reduced below standard atmospheric pressure. For example, the pressure surrounding the composition may be reduced to 100 Torr or less, or 10 Torr or less, or 1 Torr or less, or 500 mTorr or less, or 400 mTorr or less, or 300 mTorr or less, or 200 mTorr or less, or 100 mTorr or less, or 90 mTorr or less, or 80 mTorr or less, or 70 mTorr or less, or 60 mTorr or less, or 50 mTorr or less, or 40 mTorr or less, or 30 mTorr or less, or 20 mTorr or less, or 10 mTorr or less, or 5 mTorr or less, or 1 mTorr or less. In some cases, the pressure surrounding the composition is reduced to from about 150 mTorr to about 50 mTorr or less. In some cases, the pressure surrounding the composition is reduced to from about 125 mTorr to about 75 mTorr or less. In some cases, pressure surrounding the composition is reduced to from about 100 mTorr.

In various embodiments, secondary drying is performed for a period of from about 1 hour to about 30 hours or more. In some cases, primary drying is performed for a period of about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, or about 30 hours or longer. In some cases, primary drying is performed for a period of from about 5 hours to about 20 hours. In some cases, primary drying is performed for a period of from about 10 hours. In some cases, primary drying is performed for a period of from about 15 hours.

During the lyophilization process, when changing from one temperature to another temperature, the ramp rate may be about 0.5° C./minute. In various embodiments, the ramp rate may be about 0.1° C./min., about 0.2° C./min., about 0.3° C./min., about 0.4° C./min., about 0.5° C./min., about 0.6° C./min., about 0.7° C./min., about 0.8° C./min., about 0.9° C./min., or about 1° C./min. In some cases, the ramp rate may be about 2° C./min., about 3° C./min, about 4° C./min., or about 5° C./min.

In various embodiments, the lyophilization process produces a lyophilized composition with a low moisture content (e.g., less than 3% moisture). In various embodiments, the lyophilized composition has a moisture content of 3.0% or less, 2.9% or less, 2.8% or less, 2.7% or less, 2.6% or less, 2.5% or less, 2.4% or less, 2.3% or less, 2.2% or less, 2.1% or less, 2.0% or less, 1.9% or less, 1.8% or less, 1.7% or less, 1.6% or less, 1.5% or less, 1.4% or less, 1.3% or less, 1.2% or less, 1.1% or less, 1.0% or less, 0.9% or less, 0.8% or less, 0.7% or less, 0.6% or less, 0.5% or less, 0.4% or less, 0.3% or less, 0.2% or less, or 0.1% or less water as measured by Karl Fischer (KF) titration or another method (e.g., as noted below). In some embodiments, the lyophilized composition has a moisture content of from about 0.5% to about 0.8%, as measured by Karl Fischer titration or another method (e.g., as noted below). In some embodiments, the lyophilized composition has a moisture content of 0.5%, 0.55%, 0.6%, 0.65%, 0.7%, 0.75%, or 0.8%, as measured by Karl Fischer titration or another method (e.g., as noted below). In certain embodiments, a lyophilized composition has 3% or less water as measured by Karl Fischer titration.

In certain embodiments, a lyophilized composition has 2% or less water as measured by Karl Fischer titration. In certain embodiments, a lyophilized composition has 1.5% or less water as measured by Karl Fischer titration. In certain embodiments, a lyophilized composition has 1% or less water as measured by Karl Fischer titration. In certain embodiments, a lyophilized composition has 0.9% or less water as measured by Karl Fischer titration. In certain embodiments, a lyophilized composition has 0.8% or less water as measured by Karl Fischer titration. In certain embodiments, a lyophilized composition has 0.7% or less water as measured by Karl Fischer titration. In certain embodiments, a lyophilized composition has 0.6% or less water as measured by Karl Fischer titration. In certain embodiments, a lyophilized composition has 0.5% or less water as measured by Karl Fischer titration. In certain embodiments, a lyophilized composition has 0.4% or less water as measured by Karl Fischer titration. In certain embodiments, a lyophilized composition has 0.3% or less water as measured by Karl Fischer titration. In certain embodiments, a lyophilized composition has 0.2% or less water as measured by Karl Fischer titration. Other methods for determining the moisture content of the composition include, but are not limited to, loss of drying (LOD) (measures the amount of water and volatile matters in a sample when the sample is dried under specific conditions), electrolytic sensors (e.g., using a P2O5 sensor), Piezoelectric sorption, oxide sensors, aluminum oxide sensors, absorption spectroscopy, and near infrared (NIR).

Due to the low water content of a lyophilized composition as described above, the lyophilized composition may be in the form of a solid. In some cases, the solid lyophilized composition is a powder. In some cases, a lyophilized composition may facilitate storage of the composition for an extended period of time (e.g., as compared to a liquid formulation of the same composition). For instance, a lyophilized composition may be a storage stable composition, where the composition is substantially stable for an extended period of time as discussed above or herein.

Reconstituted compositions (e.g., reconstituted drug products) prepared by reconstitution of the lyophilized compositions are also encompassed within the scope of the present disclosure. Such reconstituted compositions may be administered to a subject, for example by injection or intravenously. In some embodiments, prior to administration of the reconstituted composition to a subject, a solid lyophilized composition, e.g., as described above, may be combined with a liquid to provide a liquid composition suitable for administration, for example by injection or intravenously. In some cases, prior to administration of the composition to a subject, a solid lyophilized composition may be combined with water (e.g., water for injection, WFI) or buffer/buffering agent (e.g., as described above) to provide an aqueous composition suitable for administration, for example by injection or intravenously. For instance, a lyophilized composition may be reconstituted with water (e.g., water for injection, WFI) or buffer/buffering agent (e.g., as described above) to produce a reconstituted dosage unit suitable for administration to a subject, for example by injection or intravenously.

In various embodiments, the reconstituted dosage unit has a pH compatible with physiological conditions. In some cases, the pH of the reconstituted dosage unit ranges from 6 to 8. In some cases, the pH of the reconstituted dosage unit ranges from 6.5 to 7.5. For example, the pH of the reconstituted dosage unit may range from 7 to 7.5. In some cases, the pH of the reconstituted dosage unit is 7.0. In some cases, the pH of the reconstituted dosage unit is 7.1. In some cases, the pH of the reconstituted dosage unit is 7.2. In some cases, the pH of the reconstituted dosage unit is 7.3. In some cases, the pH of the reconstituted dosage unit is 7.4. In some cases, the pH of the reconstituted dosage unit is 7.5.

The reconstituted dosage unit may include a predetermined quantity of the rAAV particles of the present disclosure calculated in an amount sufficient to produce a desired therapeutic effect in a subject. The amount of the rAAV particles in a reconstituted dosage unit that is administered to a subject may depend on the subject being treated, the severity of the affliction, and the manner of administration. For example, the reconstituted dosage unit may include a quantity of the rAAV particles to be administered as disclosed herein in a therapeutically effective amount.

Reconstitution of the lyophilized compositions discussed here may be achieved in 1 minute or less. In some cases, reconstitution of the lyophilized composition is achieved in 30 seconds or less. In some cases, reconstitution of the lyophilized composition is achieved in 20 seconds or less. In some cases, reconstitution of the lyophilized composition is achieved in 15 seconds or less. In various embodiments, reconstitution of the lyophilized composition is achieved in 60 seconds or less, 55 seconds or less, 50 seconds or less, 45 seconds or less, 40 seconds or less, 35 seconds or less, 30 seconds or less, 25 seconds or less, 20 seconds or less, 15 seconds or less, 10 seconds or less, or 5 seconds or less. In exemplary aspects, the reconstituted compositions are, or are substantially, free of visible particles.

Stability of Formulations and Compositions

The pharmaceutical formulations and compositions of the present invention exhibit high levels of stability. The term "stable," as used herein in reference to the pharmaceutical formulations, means that the AAV particles within the pharmaceutical formulations retain an acceptable degree of structure and/or function and/or biological activity after storage for a defined amount of time. A formulation may be stable even though the AAV particles contained therein do not maintain 100% of their pre-storage structure and/or function and/or biological activity after storage for a defined amount of time. Under certain circumstances, maintenance of about 90%, about 95%, about 96%, about 97%, about 98% or about 99% of the AAV particles' structure and/or function and/or biological activity after storage for a defined amount of time may be regarded as "stable."

References to stability of the pharmaceutical formulations or compositions "after" a specified period of time are intended to mean that a measurement of a stability parameter (e.g., % full capsids, vector genome titer, or average particle size) is taken at or about the end of the specific time period, and is not intended to mean that the pharmaceutical formulation or composition necessarily maintains the same degree of stability for the measured parameter thereafter. For example, reference to a particular stability after 6 months means that the measurement of stability was taken at or about 6 months after the start of the study. Additional methods for assessing the stability of AAV particles in formulation, including lyophilized compositions, are demonstrated in the Examples presented below.

Storage stability of lyophilized compositions can be assessed in reconstituted compositions prepared from the lyophilized compositions after storage for a defined amount of time.

In some cases, a stable lyophilized composition, upon reconstitution (e.g., as a reconstituted drug product) comprises an average particle size of from about 20 nm to about 40 nm, as determined by dynamic light scattering. In some cases, the average particle size of from about 25 nm to about 35 nm, as determined by dynamic light scattering. In various embodiments, the average particle size is, or is not more than, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 39 nm, or about 40 nm, as determined by dynamic light scattering.

In some cases, a stable lyophilized composition, upon reconstitution (e.g., as a reconstituted drug product) comprises an average particle size that has not changed by more than about 10%, about 9%, about 8%, about 7%, about 6%, about 5%, about 4%, about 3%, about 2%, or about 1%, as determined by dynamic light scattering after storage for a defined amount of time, relative to the average particle size in a pre-lyophilized composition.

In some cases, a stable lyophilized composition, upon reconstitution (e.g., as a reconstituted drug product) comprises a collection of rAAV particles comprising at least 80% full capsids, as determined by anion-exchange chromatography (e.g., AEX-UPLC). In some cases, the stable lyophilized composition, upon reconstitution, comprises a collection of rAAV particles comprising at least 95% full capsids, as determined by AEX-UPLC. In some cases, the collection of rAAV particles comprises, or comprises at least, 80%, 81%, 82%, 83%, 84%, 85%, 86%, 87%, 88%, 89%, 90%, 91%, 92%, 93%, 94%, 95%, 96%, 97%, 98%, or 99% full capsids, as determined by AEX-UPLC.

In some cases, a stable lyophilized composition, upon reconstitution (e.g., as a reconstituted drug product) comprises a collection of rAAV particles comprising a percentage of full capsids, as determined by AEX-UPLC, wherein the percentage of full capsids in the reconstituted composition is within 10% of a percentage of full capsids in the pharmaceutical formulation prior to lyophilization. In some cases, the percentage of full capsids in the reconstituted drug product is within 2% of a percentage of full capsids in the pharmaceutical formulation prior to lyophilization. In some cases, the percentage of full capsids in the reconstituted drug product is within 1% of a percentage of full capsids in the pharmaceutical formulation prior to lyophilization. In some cases, the percentage of full capsids in the reconstituted drug product is within 0.5% of a percentage of full capsids in the pharmaceutical formulation prior to lyophilization. In various embodiments, the percentage of full capsids in the reconstituted drug product is within 10%, within 9%, within 8%, within 7%, within 6%, within 5%, within 4.5%, within 4%, within 3.5%, within 3%, within 2.5%, within 2%, within 1.5%, within 1%, within 0.75%, within 0.5%, or within 0.25% of a percentage of full capsids in the pharmaceutical formulation prior to lyophilization, as determined by AEX-UPLC.

In some cases, a stable lyophilized composition, upon reconstitution (e.g., as a reconstituted drug product) comprises a vector genome titer, as determined by droplet digital polymerase chain reaction (ddPCR), that is within 10% of the vector genome titer present in the pharmaceutical formulation prior to lyophilization. In some cases, the vector genome titer is within 7% of the vector genome titer present in the pre-lyophilized formulation. In some cases, the vector genome titer is within 5% of the vector genome titer present in the pre-lyophilized formulation. In various embodiments, the stable lyophilized composition, upon reconstitution (e.g., as a reconstituted drug product) comprises a vector genome titer, as determined by ddPCR, that is within 10%, within 9%, within 8%, within 7%, within 6%, within 5%, within 4%, within 3%, within 2%, or within 1% of the vector genome titer present in the pharmaceutical formulation prior to lyophilization.

In any of the various embodiments discussed above or herein, storage stability of lyophilized compositions, assessed in reconstituted compositions prepared from the lyophilized compositions, can be measured after storage for a defined period of time at a specified temperature. In some cases, the period of time is 1 month. In some cases, the period of time is 3 months. In some cases, the period of time is 6 months. In various embodiments, the period of time is 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 42 months, 48 months, or 5 years or more. In various embodiments, the stability parameter may be measured after a period of time (as discussed above) stored at a temperature of −30° C., −20° C., −10° C., −5° C., 0° C., 2-8° C., 5° C., 10° C., 15° C., 20° C., or 25° C. In some cases, the storage period and temperature are 1 month at a temperature of from 2-8° C. In some cases, the storage period and temperature are 3 months at a temperature of from 2-8° C. In some cases, the storage period and temperature are 6 months at a temperature of from 2-8° C.

In some cases, a stable lyophilized composition, upon reconstitution (e.g., as a reconstituted drug product) has a storage parameter, as discussed above or herein, that remains the same, or substantially the same, as the parameter as measured in the pre-lyophilized formulation.

Exemplary Formulations and Compositions

According to one aspect of the present invention, the pharmaceutical formulation comprises (i) recombinant adeno-associated virus (rAAV) particles, (ii) a buffering agent at a concentration of from about 1 mM to about 20 mM, (iii) a first salt at a concentration of from about 10 mM to about 50 mM, (iv) a second salt at a concentration of from about 20 mM to 100 mM, (v) a sugar at a concentration of from about 1% w/v to about 10% w/v, (vi) a bulking agent at a concentration of from about 1% w/v to about 6% w/v, and (vii) a surfactant at a concentration of from about 0.001% w/v to about 0.1% w/v, wherein the formulation has a pH of from about 6.8 to about 7.8.

In some cases, the pharmaceutical formulation comprises (i) recombinant adeno-associated virus (rAAV) particles, (ii) a Tris buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles selected from the group consisting of AAV1 serotype, AAV2 serotype, AAV3 serotype, AAV4 serotype, AAV5 serotype, AAV6 serotype, AAV7 serotype, AAV8 serotype, AAV9 serotype, and AAV10 serotype, (ii) a Tris buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles of serotype AAV1, (ii) a Tris buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles of serotype AAV5, (ii) a Tris buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles of serotype AAV8, (ii) a Tris buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles of serotype AAV9, (ii) a Tris buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles, (ii) a Tris buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In some cases, the pharmaceutical formulation comprises (i) recombinant adeno-associated virus (rAAV) particles selected from the group consisting of AAV1 serotype, AAV2 serotype, AAV3 serotype, AAV4 serotype, AAV5 serotype, AAV6 serotype, AAV7 serotype, AAV8 serotype, AAV9 serotype, and AAV10 serotype, (ii) a Tris buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In some cases, the pharmaceutical formulation comprises (i) recombinant adeno-associated virus (rAAV) particles of serotype AAV1, (ii) a Tris buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In some cases, the pharmaceutical formulation comprises (i) recombinant adeno-associated virus (rAAV) particles of serotype AAV5, (ii) a Tris buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In some cases, the pharmaceutical formulation comprises (i) recombinant adeno-associated virus (rAAV) particles of serotype AAV8, (ii) a Tris buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In some cases, the pharmaceutical formulation comprises (i) recombinant adeno-associated virus (rAAV) particles of serotype AAV9, (ii) a Tris buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In some cases, the pharmaceutical formulation comprises (i) recombinant adeno-associated virus (rAAV) particles, (ii) a phosphate buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles selected from the group consisting of AAV1 serotype, AAV2 serotype, AAV3 serotype, AAV4 serotype, AAV5 serotype, AAV6 serotype, AAV7 serotype, AAV8 serotype, AAV9 serotype, and AAV10 serotype, (ii) a phosphate buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles of serotype AAV1, (ii) a phosphate buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles of serotype AAV5, (ii) a phosphate buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles of serotype AAV8, (ii) a phosphate buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles of serotype AAV9, (ii) a phosphate buffer at a concentration of from 5 mM to 15 mM, (iii) sodium chloride at a concentration of from 20 mM to 40 mM, (iv) L-arginine hydrochloride at a concentration of from 30 mM to 90 mM (v) sucrose at a concentration of from 3% w/v to 7% w/v, (vi) mannitol at a concentration of from 2% w/v to 5% w/v, and (vii) polysorbate 80 or poloxamer 188 at a concentration of from 0.005% w/v to 0.015% w/v, wherein the formulation has a pH of from 7.1 to 7.5.

In some cases, the pharmaceutical formulation comprises (i) recombinant adeno-associated virus (rAAV) particles, (ii) a phosphate buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In some cases, the pharmaceutical formulation comprises (i) recombinant adeno-associated virus (rAAV) particles selected from the group consisting of AAV1 serotype, AAV2 serotype, AAV3 serotype, AAV4 serotype, AAV5 serotype, AAV6 serotype, AAV7 serotype, AAV8 serotype, AAV9 serotype, and AAV10 serotype, (ii) a phosphate buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In some cases, the pharmaceutical formulation comprises (i) recombinant adeno-associated virus (rAAV) particles of serotype AAV1, (ii) a phosphate buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In some cases, the pharmaceutical formulation comprises (i) recombinant adeno-associated virus (rAAV) particles of serotype AAV5, (ii) a phosphate buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In some cases, the pharmaceutical formulation comprises (i) recombinant adeno-associated virus (rAAV) particles of serotype AAV8, (ii) a phosphate buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In some cases, the pharmaceutical formulation comprises (i) recombinant adeno-associated virus (rAAV) particles of serotype AAV9, (ii) a phosphate buffer at a concentration of 10 mM±1 mM, (iii) sodium chloride at a concentration of 30 mM±3 mM, (iv) L-arginine hydrochloride at a concentration of 40 mM±5 mM or 80 mM±5 mM (v) sucrose at a concentration of 5% w/v±1% w/v, (vi) mannitol at a concentration of 3.3% w/v±0.5% w/v, and (vii) polysorbate 80 or poloxamer 188 at a concentration of 0.01% w/v±0.002% w/v, wherein the formulation has a pH of 7.3±0.1.

In any of the various pharmaceutical formulations discussed above, the surfactant is polysorbate 80. In any of the various pharmaceutical formulations discussed above, the surfactant is poloxamer 188.

In various embodiment, the present disclosure provides a lyophilized composition prepared by lyophilization of any one of the pharmaceutical formulations discussed above, or a reconstituted composition (or drug product) prepared by reconstituting any of such lyophilized compositions.

Containers, Kits and Unit Dosage Forms

The present disclosure includes container and kits containing or comprising the formulations or compositions as discussed herein. In some cases, the container contains a pharmaceutical composition prior to lyophilization, a lyophilized composition, or a reconstituted composition or drug product. In some cases, the container is a glass vial. The present disclosure also includes kits comprising the container, and instructions for use (e.g., in the therapeutic uses discussed below).

In exemplary aspects, the compositions comprising AAV particles, as discussed herein, are contained in a glass or plastic container, e.g., a glass vial, or a plastic tube. In exemplary embodiments, the glass or plastic container is any one of those known in the art, or commercially available. In some cases, the present disclosure includes placing about 0.1 ml to about 25 ml (e.g., from about 1 ml to about 10 ml) of the composition comprising AAV particles into the glass or plastic container.

Providing the composition in a container may facilitate maintaining the composition as a sterile composition. For instance, the container may be configured to maintain the composition enclosed in the container in a sterile environment. As such, the container may be a sealed container, for example the container may include a seal, such as a water-tight and/or an air-tight seal. The seal may be removable from the container to allow a user access to the contents of the container. In some instances, the seal may be a frangible seal, or in other instances, the seal may be configured to allow insertion of a needle, cannula or syringe into the interior of the container without removing the seal from the container. In some cases, a seal configured to allow access to the interior of the container without removing the seal from the container may facilitate maintaining the contents of the container (e.g., the composition in the container) in a sterile environment prior to administration of the composition to a subject. Suitable materials for the seal include, for example, rubber or polymer seals, such as, but not limited to, silicone rubber, natural rubber, styrene butadiene rubber, ethylene-propylene copolymers, polychloroprene, polyacrylate, polybutadiene, polyurethane, styrene butadiene, and the like, and combinations thereof. For example, in certain embodiments, the seal is a septum pierceable by a needle, syringe, or cannula. The seal may also provide convenient access to a sample in the container, as well as a protective barrier that overlies the opening of the container. In some instances, the seal is a removable seal, such as a threaded or snap-on cap or other suitable sealing element that can be applied to the opening of the container. For instance, a threaded cap can be screwed over the opening before or after a sample has been added to the container.

In some cases, the container is a unit dosage container. A unit dosage container refers to a container that contains one or more unitary dosages for administration to a subject. In some embodiments, a unit dosage container includes a predetermined quantity of a subject composition calculated in an amount sufficient to produce a desired effect in a subject. Certain embodiments of the compositions may be provided in a unit dosage container suitable for individual administration of precise dosages. The amount of active composition administered to a subject may depend on the subject being treated, the severity of the affliction, and the manner of administration. For example, the unit dosage container may contain a quantity of the composition to be administered as disclosed herein in an amount effective to achieve the desired effect in the subject being treated. In certain instances, a unit dosage container includes a composition having a AAV in a therapeutically effective amount. In certain embodiments, the unit dosage container is a vial. In some cases, the vial is a sealed vial (e.g., as described above regarding a sealed container).

The container may be composed of any convenient material that is compatible with the AAV and other components of the composition. For example, the container can be a solid-compatible container configured to contain a solid (e.g., a lyophilized composition). In some instances, the container is a liquid-compatible container configured to contain a liquid. Containers may also be solid and liquid compatible, where the container is configured to contain solids and liquids. In some cases, a liquid in the container may be an aqueous liquid, and in these cases, the container may be compatible with aqueous compositions. By "compatible" is meant that the container is substantially inert (e.g., does not significantly react with) the liquid and/or compositions or other components in contact with the container. Examples of suitable container materials include, but are not limited to, glass and plastic. For example, the container may be composed of glass, such as, but not limited to, silicate glass, borosilicate glass, sodium borosilicate glass, fused quartz glass, fused silica glass, and the like. Other examples of suitable container materials for the container include plastics, such as, but not limited to, polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), polystyrene, and the like. In certain instances, as described above, the container is a vial, and as such may be a glass vial. As described above, the container may be a sealed container, and as such may be a sealed glass vial.

In exemplary aspects, the volume of the composition comprising AAV placed into the glass or plastic container is about 0.1 to about 25 ml, about 0.1 ml to about 10 ml, about 0.1 ml to about 5 ml, about 0.2 ml to about 6 ml, about 0.2 ml to about 5 ml, about 0.25 ml to about 5 ml, about 2 ml to about 5 ml, about 2.5 ml to about 5 ml, about 3 ml to about 5 ml, about 4 ml to about 5 ml, about 5 ml to about 10 ml, about 6 ml about 9 ml or about 7 ml to about 8 ml. In some cases, the volume is about 0.1 ml, about 0.2 ml, about 0.25 ml, about 0.3 ml, about 0.4 about 0.5 ml, about 0.6 ml, about 0.7 ml. about 0.75 ml, about 0.8 ml, about 0.9 ml, about 1 ml, about 2 ml, about 2.5 ml, about 3 ml, about 3.5 ml, about 4 ml, about 4.5 ml, about 5 ml, about 5.5 ml, about 6 ml, about 6.5 ml, about 7 ml, about 7.5 ml, about 8 ml, about 8.5 ml, about 9 ml, about 9.5 ml, or about 10 ml.

Therapeutic Uses

The pharmaceutical formulations and compositions of the present invention are useful, inter alia, for the treatment, prevention and/or amelioration of any disease or disorder treatable by gene therapy. In exemplary embodiments, the pharmaceutical compositions discussed herein can be administered to a subject in an amount effective to treat the disorder.

The compositions disclosed herein may be formulated for administration via known methods, such as intravenous administration (e.g., as a bolus or by continuous infusion over a period of time), or by injection. In certain embodiments, the AAV formulations provided herein can be administered either systemically or locally. Systemic administration includes, without limitation, intravenous administration. Local administration includes, without limitation, subcutaneous and intramuscular injection administration.

When administered to a subject, the liquid or reconstituted dosage unit may include a therapeutically effective amount of the AAV such that the reconstituted dosage unit delivers from 1E10 viral genome (or vector genome)/milliliter (vg/ml) to 5E15 vg/ml.

In certain embodiments, administration of the liquid or reconstituted dosage unit to the subject is performed according to a treatment regimen. For example, in some cases, a subject to be treated may have been prescribed a treatment regimen from a health care provider. In some cases, a treatment regimen includes a single administration of the dosage unit. In general, a subject administered an AAV drug product will develop anti-drug antibodies against the serotype of AAV administered to the subject, thereby preventing additional administration of the drug product to produce a therapeutic effect. This does not preclude the possibility that additional administrations of the same gene of interest contained within the rAAV drug product may be administered using a different AAV serotype.

In certain embodiments, reconstituted dosage units of the present disclosure can be administered prior to, concurrent with, or subsequent to other active agents for treating related or unrelated conditions, e.g., in combination therapy. Examples of such additional therapies include radiation therapies, surgical therapies and chemotherapeutic therapies. If provided at the same time as other active agents, reconstituted dosage units of the present disclosure can be provided in the same or in a different formulation. For example, concurrent therapy may be achieved by administering a reconstituted dosage unit and a pharmaceutical Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Pre-Lyophilization Formulation Screening Study

This study was designed to screen for potential formulations that are suitable for lyophilization, and that have liquid stability for up to 2 days at 25° C.

Approximately 3 mL of each of the formulations shown in Table 1 were prepared. In a laminar flow hood, each formulation was filter-sterilized using a 0.2 μm filter and dispensed into a 2R RTU glass vial for a target fill volume of 0.7 mL. All vials were sealed with a rubber stopper. A minimum of two vials of each formulation was prepared.

TABLE 1

| | | | | | | | | |
|---|---|---|---|---|---|---|---|---|
| | | | Formulations | | | | | |
| Formulation | AAV8, vg/mL | Phosphate, mM | % Sucrose, w/v | % P188, w/v | Mannitol, mM (3.3% w/v) | NaCl, mM | L-Arginine HCL, mM | pH |
| F1 | 1.00E+13 | 10 | 1.2 | 0.005 | 180 | 80 | 0 | 7.3 |
| F2 | 1.00E+13 | 10 | 1.2 | 0.005 | 180 | 50 | 0 | 7.3 |
| F3 | 1.00E+13 | 10 | 1.2 | 0.005 | 180 | 30 | 0 | 7.3 |
| F4 | 1.00E+13 | 10 | 1.2 | 0.005 | 180 | 30 | 80 | 7.3 |
| F5 | 1.00E+13 | 10 | 1.2 | 0.005 | 180 | 30 | 50 | 7.3 |
| F6 | 1.00E+13 | 10 | 1.2 | 0.005 | 180 | 30 | 30 | 7.3 |
| F7 | 1.00E+13 | 10 | 5.0 | 0.005 | 180 | 30 | 80 | 7.3 |
| F8-1 | 1.00E+13 | 10 | 5.0 | 0.005 | 180 | 0 | 110 | 7.3 | composition having at least one other active agent, such as a chemotherapeutic agent, which in combination provide a therapeutically effective dose, according to a particular treatment regimen. Administration of separate pharmaceutical compositions can be performed simultaneously or at different times (e.g., sequentially, in either order, on the same day, or on different days), as long as a therapeutically effective effect of the combination of these substances is caused in the subject undergoing therapy.

Accordingly, aspects of the present disclosure further include combination therapies. By combination therapy is meant that a AAV composition (e.g., as described herein) can be used in a combination with another therapeutic agent to treat a single disease or condition. In certain embodiments, an AAV formulation or composition of the present disclosure can be administered concurrently with the administration of another therapeutic agent. In certain embodiments, an AAV formulation or composition of the present disclosure can be administered prior or subsequent to administration of another therapeutic agent. In certain embodiments, the combination therapy includes two or more AAV compositions of different serotypes and/or containing different genes of interest.

EXAMPLES

The following examples are put forth so as to provide those of ordinary skill in the art with a complete disclosure and description of how to make and use the methods and compositions of the invention, and are not intended to limit the scope of what the inventors regard as their invention.

Particle size distribution by dynamic light scattering (DLS) was performed on a Zetasizer Ultra system (Malvern, Westborough, MA) using 90 degree side scatter with a ZEN2112 low-volume quartz cuvette. Five replicate measurements were collected per sample with 10 acquisitions each for 10 seconds for each replicate measurement.

The data demonstrated that sucrose and mannitol are compatible with AAV8 and did not induce the formation of AAV8 aggregates. Formulations F1, F4 and F7 showed comparable dynamic light scatttering (DLS) results (~25 nn) for both t=0 and 2 days at 25° C. and 60% relative humidity (other samples showed possible reversible aggregation). The DLS assay demonstrated that all formulations are stable after exposure to 25° C./60% RH for 2 days. In addition, no apparent recovery loss (by ddPCR) or purity change (empty to full ratio of capsids by AEX-U PLC) was observed after incubation for 2 days at 25° C./60% RH for formulation F7.

Example 2: Lyophilization Feasibility Study

This study was designed to evaluate the lyophilization process feasibility of seven formulations proposed for AAV8 lyophilization process development.

Sucrose was used as the cryo-protectant, and mannitol (3.3% w/v) was used as the bulking agent. Formulations with varying levels of L-Arginine HCl and NaCl at (0 mM, 30 mM, 50 mM and 80 mM) with two concentrations of sucrose (1.2% w/v and 5% w/v) and 0.005% w/v P188 were used to evaluate the lyophilization design. The seven formulations evaluated in this study are shown in Table 2.

TABLE 2

| | | | % | % | | | | |
| Formulation | AAV8, vg/mL | Phosphate, mM | Sucrose, w/v | P188, w/v | Mannitol, mM | NaCl, mM | L-Arginine HCL, mM | pH |
| --- | --- | --- | --- | --- | --- | --- | --- | --- |
| F1 | 1.00E+13 | 10 | 1.2 | 0.005 | 180 | 80 | 0 | 7.3 |
| F2 | 1.00E+13 | 10 | 1.2 | 0.005 | 180 | 50 | 0 | 7.3 |
| F3 | 1.00E+13 | 10 | 1.2 | 0.005 | 180 | 30 | 0 | 7.3 |
| F4 | 1.00E+13 | 10 | 1.2 | 0.005 | 180 | 30 | 80 | 7.3 |
| F5 | 1.00E+13 | 10 | 1.2 | 0.005 | 180 | 30 | 50 | 7.3 |
| F6 | 1.00E+13 | 10 | 1.2 | 0.005 | 180 | 30 | 30 | 7.3 |
| F7 | 1.00E+13 | 10 | 5.0 | 0.005 | 180 | 30 | 80 | 7.3 |

Lyophilzation Formulations

In a laminar flow hood, each formulation was filter-sterilized using a 0.2 μm filter and dispensed into a 2 mL glass vial for a target fill volume of 0.4 mL. All vials were sealed with a rubber stopper. A minimum of 10 vials of each formulation was prepared. Tc collapse temperature or Teu eutectic temperature of each formulation will be measured by the freeze drying microscope.

The load for each lyophilization cycle contained 70 2 mL glass vials; 10 vials for each of the formulations F1-F7. Each formulation was grouped together. The vials were evaluated for moisture content, cake appearance, and Tg (glass transition) analysis. Dynamic light scattering was used to detect aggregation, the major degradation pathway for AAV products.

The lyophilization cycle is shown in Table 3, below.

TABLE 3

Lyophilization Cycle

| | |
| --- | --- |
| Initial Hold at: | 5° C. for 60 minutes |
| Ramp rate for freezing: | 0.5° C./minute |
| Hold at: | −45° C. for 60 minutes |
| Ramp rate for heating (annealing): | 0.5° C./min |
| Annealing: | −20° C. for 6 hours |
| Ramp rate for freezing: | 0.5° C./min |
| Hold at: | −45° C. for 120 minutes |
| Vacuum set point: | 100 mTorr |
| Ramp rate for heating (primary drying): | 0.3° C./min |
| Temperature of primary drying: | −26° C. |
| Length of primary drying: | 50 hours |
| Temperature of secondary drying: | 35° C. 100 mTorr |
| Ramp rate of secondary drying: | 0.3° C./minute |
| Length of secondary drying: | 10 hours |
| Stoppering under vacuum: | 608,000 mTorr (80% atmospheric pressure) |
| Back fill gas required? | Yes     Gas: Nitrogen |

Freeze drying experiments were performed using FTS LyoStar™ 3 freeze dryer (SP Scientific, Stone Ridge, NY). Ready-to-use (RTU) Type I glass vials (SCHOTT, Mülheim, Germany), as noted above, were placed in the lyophilization shelf. Two wire thermocouples (Omega, Norwalk, CT) were used to monitor the placebo product temperature profiles throughout the lyophilization process. Samples were initially incubated at 5° C. for 60 minutes, cooled from 5° C. to −45° C. at a ramp rate of 0.5° C./min followed by an isothermal hold for 60 minutes. Annealing was at −20° C. for 6 hours at a ramp rate of 0.5° C./min, cooled back to −45° C. at a ramp rate of 0.5° C./min followed by a hold for 60 minutes. Primary drying was at −26° C. under 100 mTorr chamber pressure for 50 hours, followed by secondary drying at 35° C. under 100 mTorr for 10 hours with a heating ramp rate of 0.3° C./min for both primary and secondary drying. At the end of the lyophilization cycle samples were backfilled with nitrogen gas at 80% atmospheric pressure, capped with 13 mm Flurotec® chlorobutyl stoppers, and sealed with 13 mm aluminum flip-off seals (West, Jersey Shore, PA).

The color and cake appearance of the lyophilized products were assessed by visual inspection.

The glass transition temperature Tg' of the maximally freeze-concentrated solution of the liquid formulations and the glass transition temperature Tg of the solid lyophilized formulations were determined on DSC2500 (TA Instruments, New Castle, DE). To determine the Tg', 40 uL of sample solutions were pipetted into the Tzero pan and sufficiently sealed with Tzero Hermetic lid. To determine the Tg, the lyophilized samples were ground and prepared in a humidity-controlled room to minimize introduction of moisture into the samples during sample preparation. The sample powder was then transferred into the Tzero pan and sufficiently sealed with the Tzero Hermetic lid. The samples were equilibrated at −80° C., then held isothermal for 5 minutes before ramping 2° C./min to 25° C. with a modulation of 0.5° C. every 60 seconds. Data analysis was carried out in TRIOS.

The collapse temperatures (Tc) of the formulations were determined on a Lyostat 3 freeze drying microscope (Linkam Scientific, Waterfield, UK) equipped with a polarizing filter and an Olympus camera. About 5 uL of sample solution was loaded onto a glass cover slip placed in a cooling-stage under the microscope. The sample was first frozen to −45° C. followed by a 1° C./minute heating ramp to 0° C. under vacuum (100 mTorr). Images were acquired and exported using the Linsys32 software and used to determine the Tc.

Residual moisture content of the lyophilized samples was determined using the Vapor Pro RX Moisture Analyzer and dry air generator (Arizona Instrument, Chandler, AZ). Prior to analysis, the lyophilized cakes were broken up into small pieces in the sealed glass vials. The air flow rate was set at 75 mL/min and drying temperature at 75° C. To calculate the percent residual moisture content, the measured weight of the residual moisture was divided by the weight of the lyophilized cake.

Figure 2:
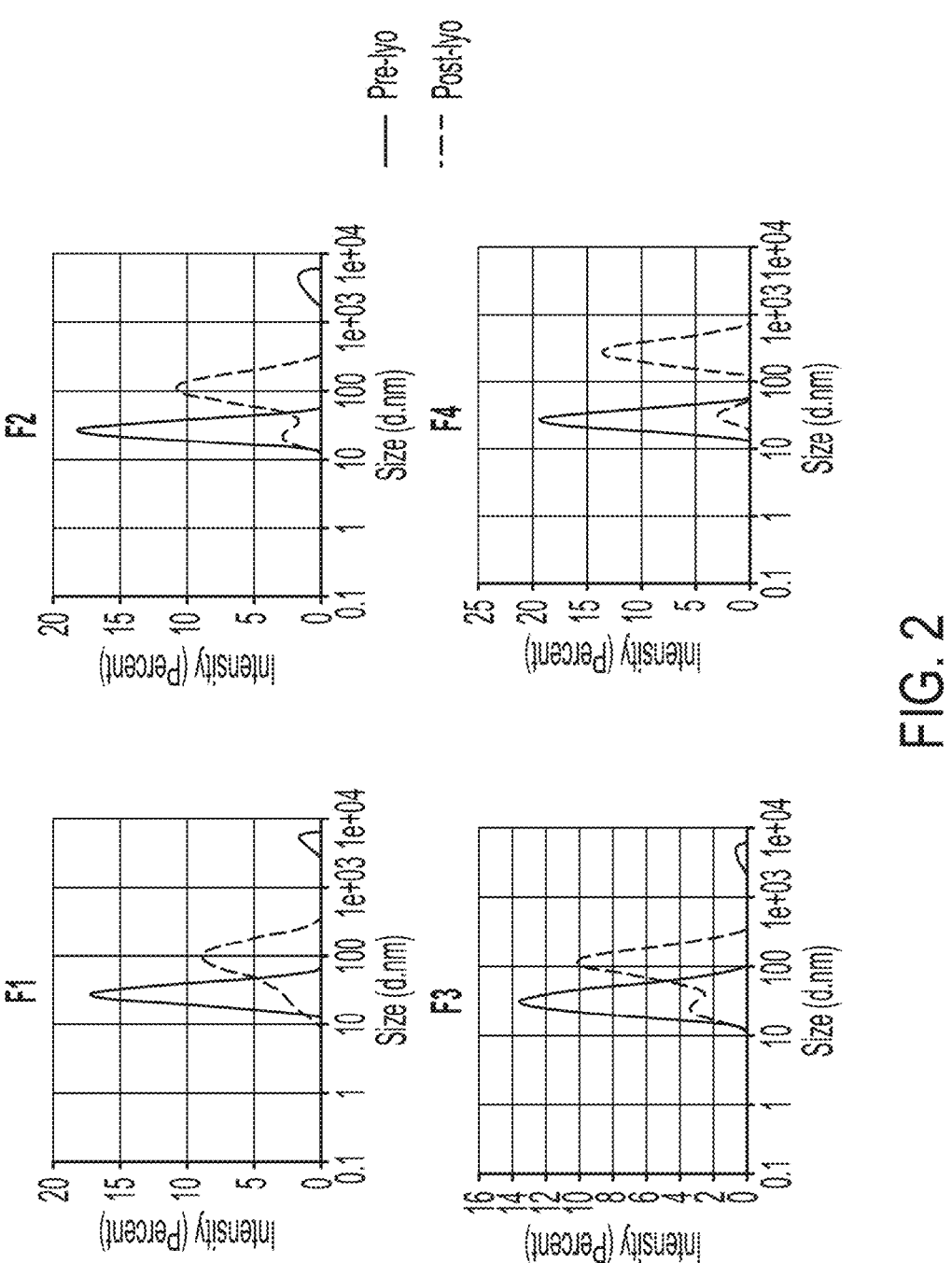
FIG. 2 shows the size distribution profile of seven formulations evaluated in a lyophilization feasibility study (Example 2). The darker peak at left in all panels except F7 represents the pre-lyophilization particle size, while the lighter peak at right in all panels except F7 represents the post-lyophilization particle size. The two peaks align with one another in the F7 panel.
Figure 2:
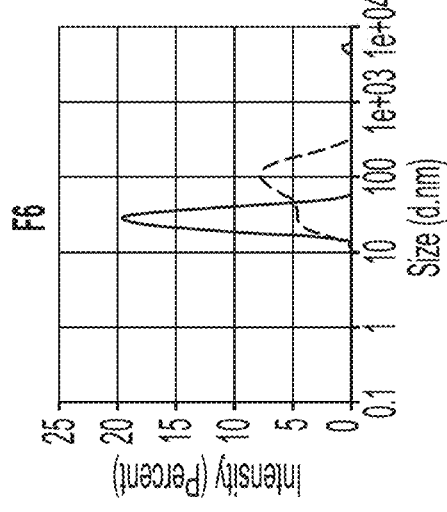
Figure 2:
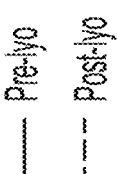
Figure 2:
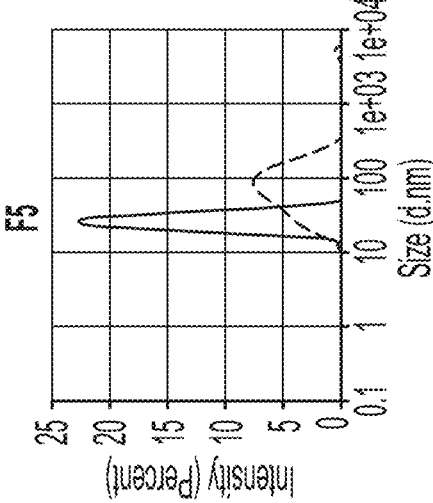
Figure 2:
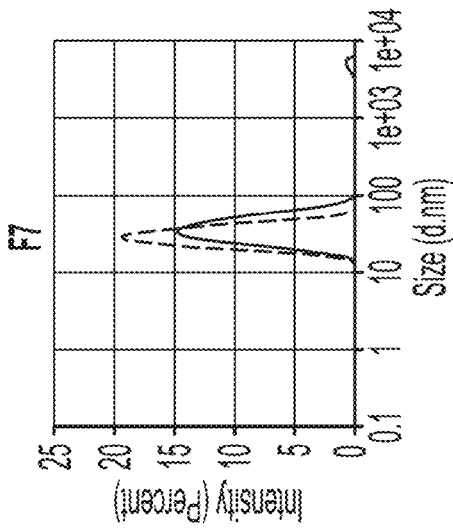

Particle size distribution by dynamic light scattering (DLS) was performed on a Zetasizer Ultra system (Malvern, Westborough, MA) using 90 degree side scatter with a ZEN2112 low-volume quartz cuvette. Five replicate measurements were collected per sample with 10 acquisitions each for 10 seconds for each replicate measurement. The results of the DLS assay for each of the seven formulations are shown in FIG. 2. Among the seven formulations evaluated, F7 was the only formulation that demonstrated minimal change in the size distribution profile compared to the pre-lyophilization sample.

Example 3: Buffer Screening Study

An evaluation of stability of formulations of rAAV8 using Tris buffer vs. sodium phosphate buffer was performed. The average particle size to identify aggregates was determined both pre- and post-lyophilization, the % of full capsids was determined pre- and post-lyophilization, and the titer of the viral genome was determined pre- and post-lyophilization. Lyophilization was performed as discussed above in Example 2.

The rAAV8 capsids contained a gene of interest (GOI) for therapeutic applications. The rAAV8 vectors were produced by triple transfection of HEK293 cells at Regeneron Pharmaceuticals (Tarrytown, NY).

The sodium phosphate formulation contained 1.00E13 vg/mL rAAV8-GOI, 10 mM sodium phosphate at pH 7.3, 0.005% w/v P188, 5% w/v sucrose, 3.3% w/v mannitol, 30 mM NaCl, and 80 mM L-arginine hydrochloride. The Tris formulation contained 1.00E13 vg/mL rAAV8-GOI, 10 mM Tris buffer at pH 7.3, 0.005% w/v P188, 5% w/v sucrose, 3.3% w/v mannitol, 30 mM NaCl, and 80 mM L-arginine hydrochloride.

Particle size distribution by dynamic light scattering (DLS) was performed on a Zetasizer Ultra system (Malvern, Westborough, MA) using 90 degree side scatter with a ZEN2112 low-volume quartz cuvette. Five replicate measurements were collected per sample with 10 acquisitions each for 10 seconds for each replicate measurement.

Empty to full capsid ratio was determined by anion exchange ultra-performance liquid chromatography (AEX-UPLC) on a Waters Acquity UPLC H-Class system with PDA and FLR detectors (Waters, Milford, MA) and a CIMac AAV empty/full 0.1 mL, 1.3 μm analytical column (BIA Separation, Slovenia). Empty and full capsids were eluted at 0.8 mL/min using a linear gradient containing bis-tris propane and tetramethylammonium chloride at pH 8.5. Peak identification and integration were carried out using Waters Empower chromatography data system.

Vector genome titer was quantified using the QX200 Droplet Digital PCR (ddPCR) system (BioRad, Hercules, CA). AAV samples were prepared in triplicate and digested with DNase I (Ambion Part No. AM2224) to eliminate non-encapsulated DNA, followed by digestion with proteinase K (Invitrogen Part No. 25530049) to disrupt the capsids. ddPCR master mix containing the primer and probe set was then added and mixed with the reaction mixture. A 22 μL aliquot was subsequently removed and introduced to the droplet generator for droplet partitioning. Following droplet generation, vector genome DNA contained in the droplets was amplified with PCR and analyzed with QuantaSoft software on the droplet reader.

The results of the stability evaluations pre- and post-lyophilization are shown in Table 5, below.

TABLE 5

| Stability Assessments of Sodium Phosphate vs Tris Buffer | | | | |
| --- | --- | --- | --- | --- |
| Formulation | DLS Z-Avg, (nm) | AEX % Full Capsids | ddPCR Titer (vg/mL) | % Titer Recovery |
| NaPB - F7 (Pre-Lyo) | 25 | 97.4 | 6.04E+12 | 100.0 |
| NaPB - F7 (Post-Lyo) | 35 | 95.7 | 5.48E+12 | 90.6 |
| Tris - F1 (Pre-Lyo) | 27 | 97.8 | 8.20E+12 | 100.0 |
| Tris - F1 (Post-Lyo) | 31 | 97.7 | 7.69E+12 | 93.7 |

The results of the stability evaluation showed superior results with the Tris buffer in following lyophilization. The differences in average particle size are believed to be the result, at least in part, of nanobubbles in the reconstituted compositions rather than aggregation of the AAV particles, as discussed in greater detail below in Example 7.

Example 4: Evaluation of Sugar and Salt Concentrations

An evaluation of sucrose concentration, as well as the concentration of NaCl and arginine HCL was undertaken to determine the impact on rAAV8-GOI stability. The eight formulations shown in Table 6, below, were evaluated. Lyophilization of these eight formulations was performed as discussed above in Example 2.

TABLE 6

| | | | | | | | | |
| --- | --- | --- | --- | --- | --- | --- | --- | --- |
| | | | Formulations | | | | | |
| Formulation | AAV8, vg/mL | Phosphate, mM | % Sucrose w/v | % P188, w/v | Mannitol, w/v | NaCl, mM | L-Arginine HCL, mM | pH |
| F1 | 1.00E+13 | 10 | 1.2 | 0.005 | 3.3 | 80 | 0 | 7.3 |
| F2 | 1.00E+13 | 10 | 1.2 | 0.005 | 3.3 | 50 | 0 | 7.3 |
| F3 | 1.00E+13 | 10 | 1.2 | 0.005 | 3.3 | 30 | 0 | 7.3 |
| F4 | 1.00E+13 | 10 | 1.2 | 0.005 | 3.3 | 30 | 80 | 7.3 |
| F5 | 1.00E+13 | 10 | 1.2 | 0.005 | 3.3 | 30 | 50 | 7.3 |
| F6 | 1.00E+13 | 10 | 1.2 | 0.005 | 3.3 | 30 | 30 | 7.3 |
| F7 | 1.00E+13 | 10 | 5.0 | 0.005 | 3.3 | 30 | 80 | 7.3 |
| F8-1 | 1.00E+13 | 10 | 5.0 | 0.005 | 3.3 | 0 | 110 | 7.3 |

Both pre- and post-lyophilization particle size distribution by dynamic light scattering (DLS) was performed on a Zetasizer Ultra system (Malvern, Westborough, MA) using 90 degree side scatter with a ZEN2112 low-volume quartz cuvette. Five replicate measurements were collected per sample with 10 acquisitions each for 10 seconds for each replicate measurement.

Results are shown in Table 7, below.

TABLE 7

Particle Size Distribution of Formulations Pre- and Post-Lyophilization

| Formulation | Variant Excipients | Z-Avg by DLS (nm) Pre-Lyo AAV | Z-Avg by DLS (nm) Post-Lyo AAV |
|---|---|---|---|
| F1 | 80 mM NaCl, 1.2% sucrose | 29.8 | 59.3 |
| F2 | 50 mM NaCl, 1.2% sucrose | 43.3 | 70.8 |
| F3 | 30 mM NaCl, 1.2% sucrose | 32.0 | 67.6 |
| F4 | 30 mM NaCl, 80 mM L-Arg, 1.2% sucrose | 25.1 | 164.4 |
| F5 | 30 mM NaCl, 50 mM L-Arg, 1.2% sucrose | 27.1 | 54.2 |
| F6 | 30 mM NaCl, 30 mM L-Arg, 1.2% sucrose | 30.2 | 54.6 |
| F7 | 30 mM NaCl, 80 mM L-Arg, 5% sucrose | 24.7 | 34.9 |
| F8-1 | 110 mM L-Arg HCl, 5% sucrose | 43.0 | 116.4 |

Formulation F7, with 30 mM NaCl, 80 mM L-Arg HCl, and 5% sucrose, showed the least particle size increase of the formulations tested. This formulation also demonstrated good in-solution stability for 2 days at 25° C. without signs of aggregation. The observed differences in the particle size distribution are believed to be the result, at least in part, of nanobubbles in the reconstituted compositions rather than aggregation of the AAV particles, as discussed in greater detail below in Example 7.

An analysis of residual moisture content in formulation F7, post-lyophilization, found a moisture content of 0.7%. Residual moisture content was determined using the Vapor Pro RX Moisture Analyzer and dry air generator (Arizona Instrument, Chandler, AZ). Prior to analysis, the lyophilized cake was broken up into small pieces in the sealed glass vials. The air flow rate was set at 75 mL/min and drying temperature at 75° C. To calculate the percent residual moisture content, the measured weight of the residual moisture was divided by the weight of the lyophilized cake.

titer recovery relative to that achieved with the control formulation. This observation was unexpected based on an assumption that salts may not be an effective stabilizer for proteins in the lyophilized drug products because they crystalize during freeze drying and do not remain in the amorphous matrix, which is a prerequisite for stabilizing proteins in the dried form. These results confirmed that salts with about 110 mM total ionic strength provide stabilizing effects for lyophilized AAV8 formulations.

Example 5: Impact of Bulking Agent and Concentration on Lyophilized Product

An evaluation of the impact of mannitol on an rAAV8-GOI lyophilized product, as well as concentrations of mannitol, sucrose, and salts was undertaken.

Formulations with and without mannitol were lyophilized, and assessed for appearance, reconstitution time, and residual moisture content, as discussed above in Example 2. The two evaluated formulations are shown in Table 8, below, along with the results of the assessments.

TABLE 8

Impact of Bulking Agent on Lyophilized Formulations

| Formulation | Description | Cake Appearance | Recon Time (sec) | Post Recon Visual | % Moisture |
|---|---|---|---|---|---|
| BA1 | 1E13 vg/ml AAV8, 10 mM sodium phosphate at pH 7.3, 80 mM NaCl, 0.01% w/v P188, 10% w/v sucrose | off-white uniform cake; severe shrinkage | 58 | Clear, free of visible particles | 2.0 |
| BA2 | 1E13 vg/ml AAV8, 10 mM sodium phosphate at pH 7.3, 80 mM NaCl, 0.01% w/v P188, 5% w/v sucrose, 3.3% w/v mannitol | off-white uniform cake; no apparent reduction in volume with slight shrinkage at cake bottom | 15 | Clear, free of visible particles | 0.7 |

Figure 6A:
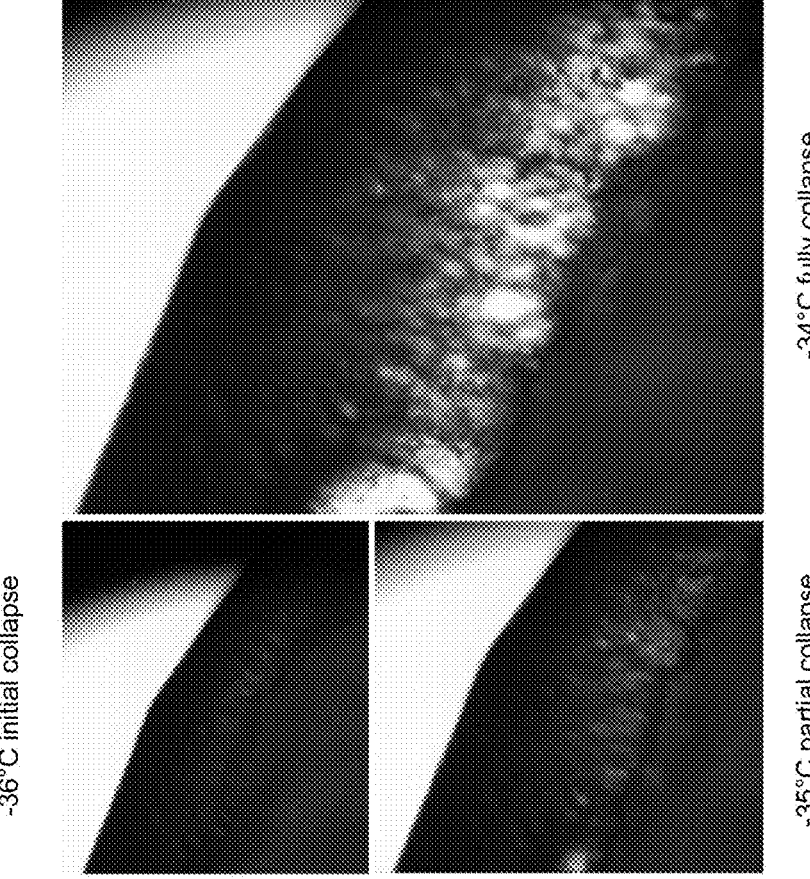
FIGS. 6A and 6B show results of thermal characterization of an AAV8 formulation.
Figure 6B:
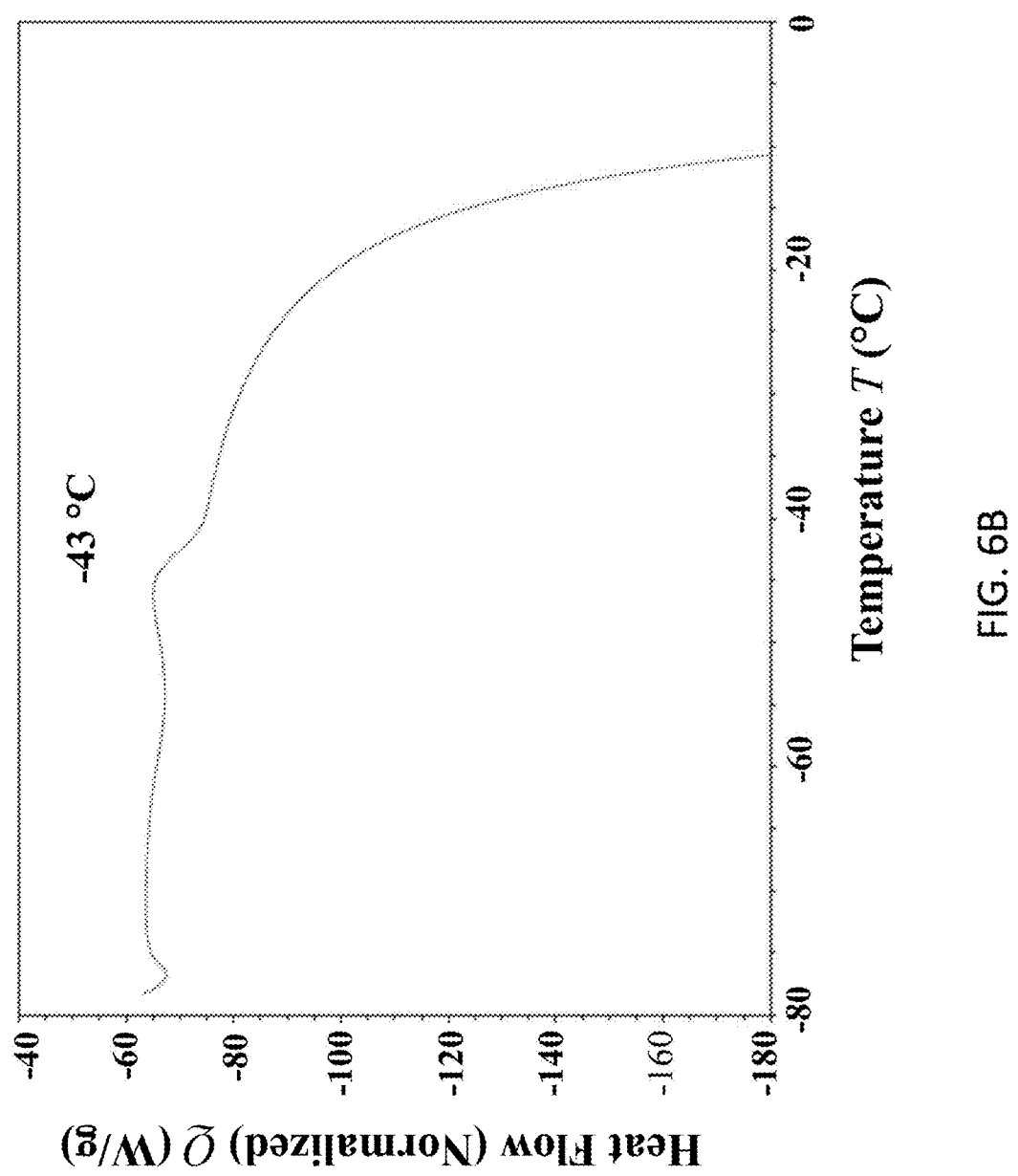

The Tc and Tg' of the formulation (F7) were measured using Freeze Drying Microscopy and DSC, determined as −34° C. and −43° C., respectively. Results are shown in FIGS. 6A and 6B.

Figure 5:
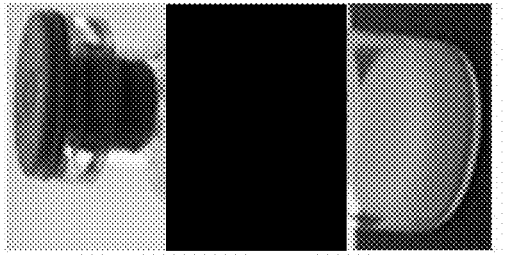
FIG. 5 shows the cake structure of each of two formulations in the absence of mannitol (BA1) and in the presence of mannitol (BA2) following lyophilization. The BA2 formulation results in an elegant cake appearance without the defects resulting from the BA1 formulation.
Figure 5:
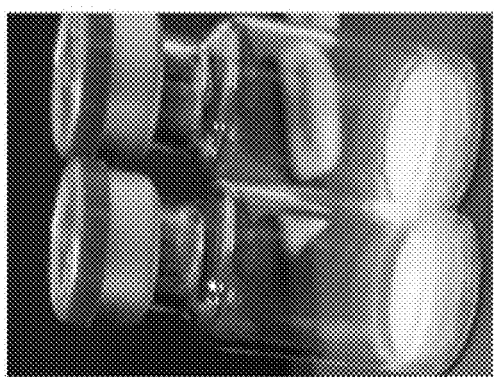
Figure 9B:
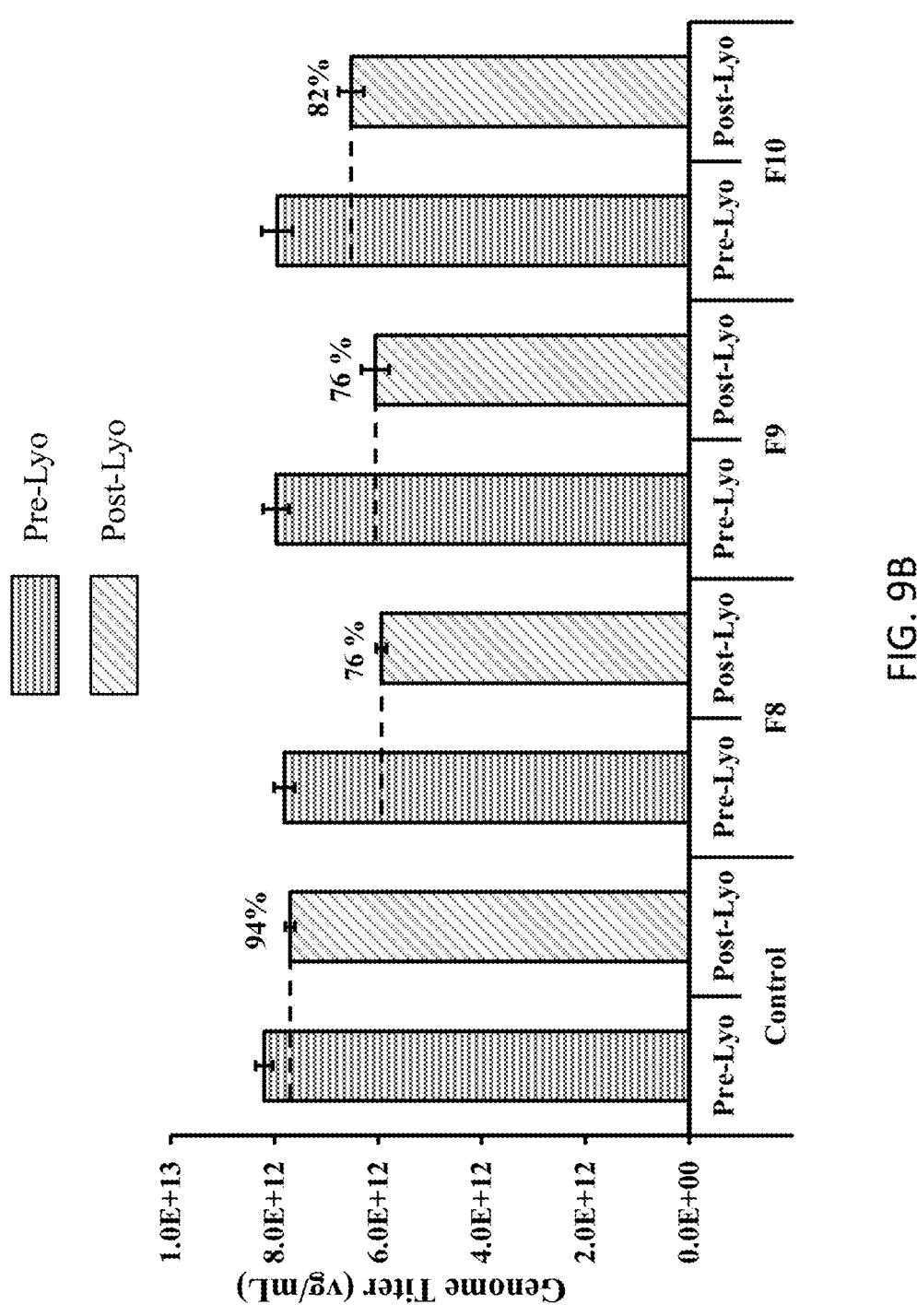
Figures 10A, 10B, 10C:
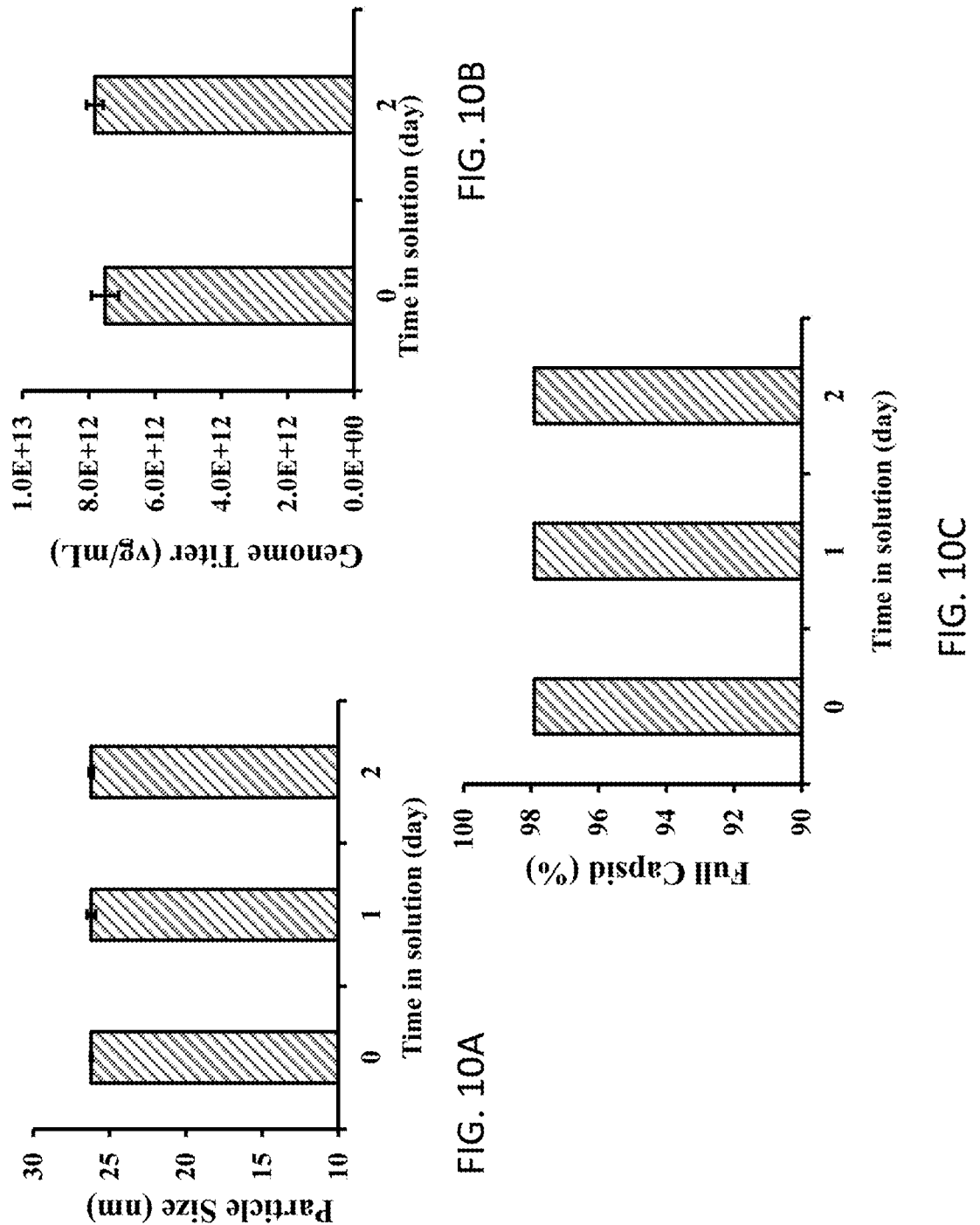
FIGS. 10A, 10B and 10C show results of in-solution stability of an AAV8 formulation at 25° C. AAV8 vectors were formulated in a formulation containing $1 \times 10^{13}$ vg/mL AAV8, 10 mM tris, 30 mM NaCl, 80 mM L-Arg HCl, 5% w/v sucrose, 3.3% w/v mannitol, 0.01% w/v P188, pH 7.3 and then stored at 25° C. for 2 days.
Figures 11A, 11B, 11C:
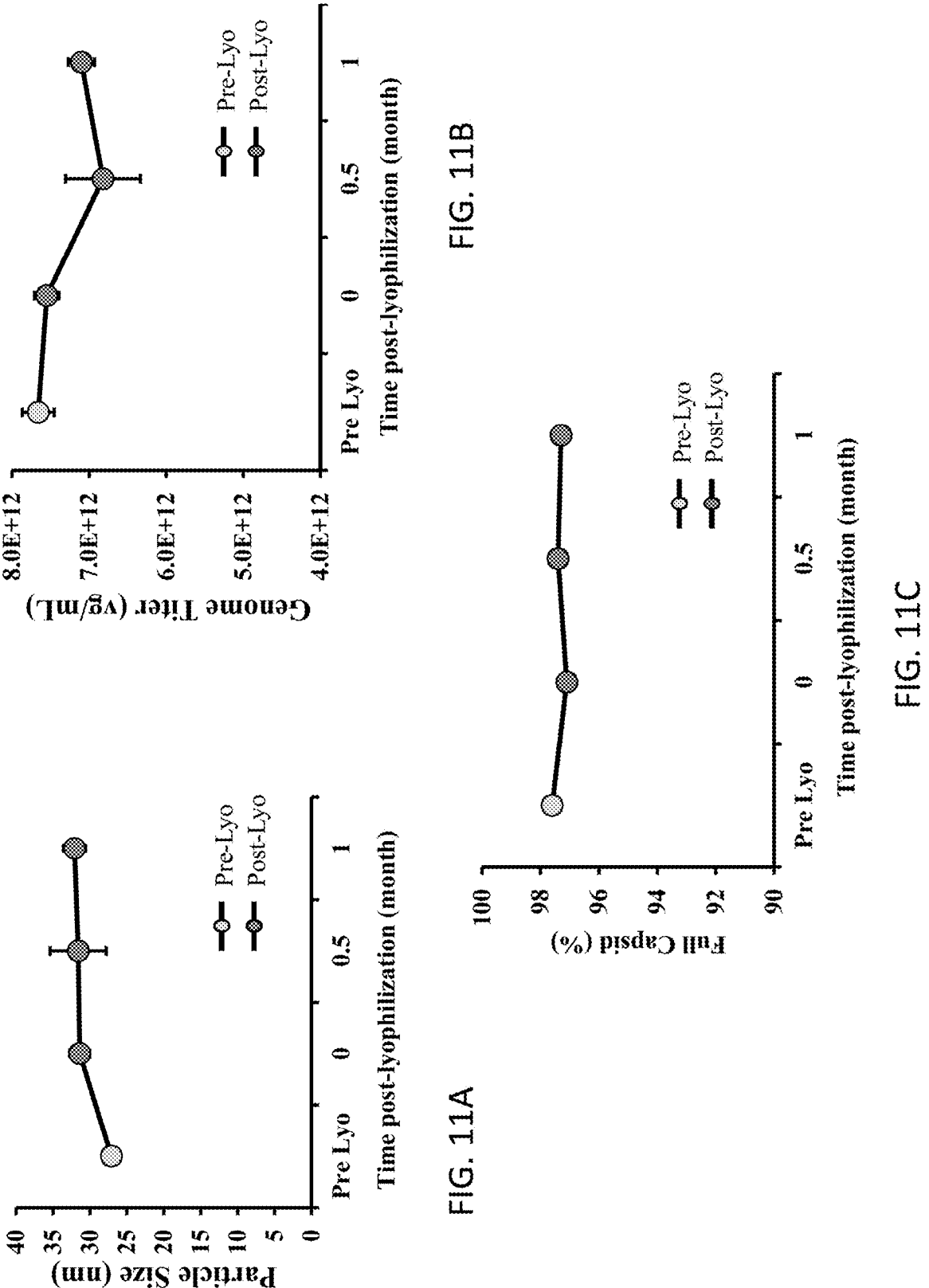
FIGS. 11A, 11B and 11C show results of stability of lyophilized AAV8 products in the formulation ($1 \times 10^{13}$ vg/mL AAV8, 10 mM tris, 30 mM NaCl, 80 mM L-Arg HCl, 5% w/v sucrose, 3.3% w/v mannitol, 0.01% w/v P188, pH 7.3) at 25° C. Results from the pre-lyophilization formulation are illustrated with light colored dots, and results from the reconstituted post-lyophilization product are illustrated with dark colored dots.

As shown in FIGS. 9A and 9B, reducing the total ionic strength in the formulation to 80 mM led to a profound reduction (~18%) in post-lyophilization vg titer recovery. Although addition of 2 mM magnesium chloride helped to improve vg titer recovery by about 6%, it failed to demonstrate comparable stabilizing effect in post-lyophilization vg The presence of mannitol improved cake appearance and reduced residual moisture content, as shown in FIG. 5.

The impact of varying concentrations of mannitol, sucrose, NaCl, Arginine-HCl and MgCl2 on rAAV8-GOI formulations was also evaluated. The six evaluated formulations are shown in Table 9, below. All formulations contained 1E13 AAV8-GOI, 0.02% w/v P188, and 10 mM Tris at pH of 7.3.

TABLE 9

Sucrose/Mannitol and Salt Screening Study Formulations

| Formulation | Mannitol (% w/v) | Sucrose (% w/v) | NaCl (mM) | Arg-HCl (mM) | MgCl$_2$ (mM) |
|---|---|---|---|---|---|
| SM1 | 7.0 | 5.0 | 80 | 0 | 0 |
| SM2 | 7.0 | 5.0 | 80 | 0 | 2 |
| SM3 | 7.0 | 5.0 | 40 | 40 | 0 |
| SM4 | 7.0 | 7.0 | 80 | 0 | 0 |
| SM5 | 0 | 10.0 | 80 | 0 | 0 |
| SM6 | 3.3 | 5.0 | 80 | 0 | 0 |

The results are expected to show that varying the concentrations of these components yields comparable stability results.

Example 6: Surfactant Screening Study

An evaluation of stability of formulations of rAAV8 using poloxamer 188 (P188) or polysorbate 80 (PS80), at varying concentrations, was performed. The average particle size to identify aggregates was determined both pre- and post-lyophilization, the % of full capsids was determined pre- and post-lyophilization, and the % recovery of the viral genome was determined pre- and post-lyophilization, as discussed above in Example 3. Lyophilization was performed as discussed above in Example 2.

In a first study, three concentrations of P188 were evaluated in formulations containing 1E13 vg/mL of rAAV8-GOI, 10 mM sodium phosphate at pH 7.3, 5% w/v sucrose, 3.3% w/v mannitol, 30 mM NaCl, and 80 mM L-Arg-HCl. The results are shown below in Table 10.

TABLE 10

Varying Concentrations of P188 on Lyophilized Formulation Stability

| Formulation (P188 Conc.) | Z-Avg (nm) Pre-Lyo | Z-Avg (nm) Post-Lyo | % Full Capsids Pre-Lyo | % Full Capsids Post-Lyo |
|---|---|---|---|---|
| S1 0.005% w/v | 27.3 | 30.6 | 97.8 | 97.7 |
| S2 0.01% w/v | 27.0 | 29.8 | 97.6 | 97.3 |
| S3 0.02% w/v | 27.2 | 30.0 | 97.6 | 97.4 |

In a second study, the effects of using PS80 in place of P188 were evaluated. Each of the formulations containing 1E13 vg/mL of rAAV8-GOI, 10 mM sodium phosphate at pH 7.3, 5% w/v sucrose, 3.3% w/v mannitol, 30 mM NaCl, and 80 mM L-Arg-HCl, and either 0.005% w/v P188 or 0.005% w/v PS80. The results are shown below in Table 11.

TABLE 11

Variation of Surfactant

| Formulation | Z-Avg (nm) Pre-Lyo | Z-Avg (nm) Post-Lyo | % Full Capsids Pre-Lyo | % Full Capsids Post-Lyo |
|---|---|---|---|---|
| P188 | 27.3 | 32.2 | 97.9 | 97.6 |
| PS80 | 26.4 | 27.9 | 97.9 | 97.6 |

Figure 4:
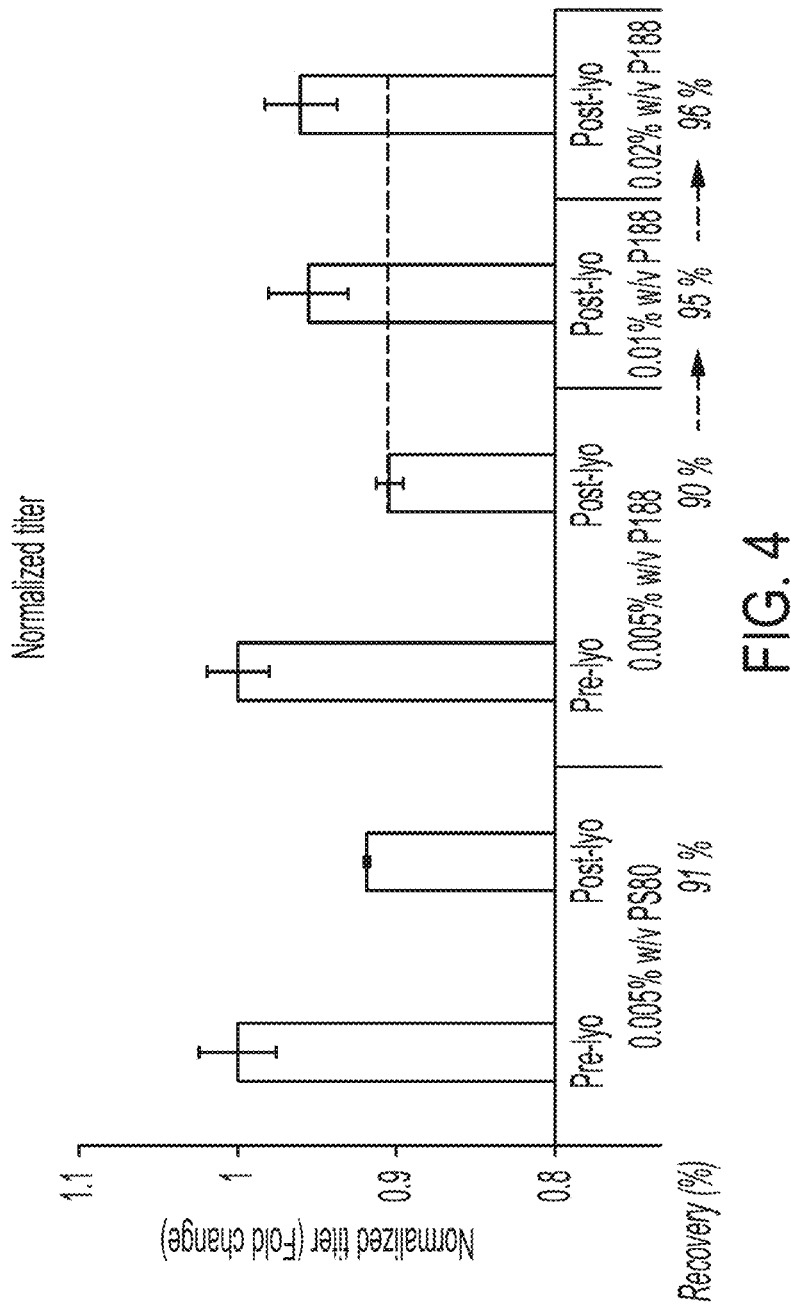
FIG. 4 shows the impact of surfactant concentration in the AAV formulations on AAV titer recovery rates. As illustrated, polysorbate 80 and poloxamer 188 showed comparable recovery rates at 0.005% w/v in the tested formulations, and increasing the concentration of the surfactant (P188) to 0.01% w/v improved the recovery rate. Further increasing the surfactant concentration to 0.2% w/v did not significantly change the recovery rate from that observed with 0.01% w/v.

In a third study, recovery rates at different concentrations of surfactant were evaluated. Each of the formulations contained 1E13 vg/mL of rAAV8-GOI, 10 mM sodium phosphate at pH 7.3, 5% w/v sucrose, 3.3% w/v mannitol, 30 mM NaCl, and 80 mM L-Arg-HCl, and varying surfactants/concentrations. Two different types of nonionic surfactant (PS80 and P188 at 0.005% w/v), as well as different concentrations of P188 (0.005, 0.01, and 0.02% w/v) were tested. As shown in FIG. 4, formulations with both 0.005% PS80 and P188 showed similar levels of recovery loss in post-lyophilization t=0 samples (91% and 90%, respectively), suggesting the observed recovery loss was not associated with specific type of nonionic surfactant. However, increasing the concentration of surfactant from 0.005% to 0.01%, and 0.02% w/v resulted in increased post-lyophilization recovery (90, 95, and 96%, respectively), suggesting the observed recovery loss was likely due to AAV adsorption to type I glass vials during the freeze-drying process. The largest increase in post-lyophilization recovery was observed when increasing P188 concentration from 0.005% to 0.01% and further increasing surfactant concentration seemed to have minimal impact. Thus, a surfactant concentration at approximately 0.01% w/v will be sufficient for mitigating AAV adsorption to glass vials in the titer range tested.

Example 7: Stability of rAAV Lyophilized Formulations at 2-8° C.

Six formulations were prepared (three placebo and three with rAAV8) to evaluate the stability of the lyophilized drug product over time. Lyophilization was performed as discussed above in Example 2, except that the length of secondary drying was increased to 10 hours. The formulations are identified in Table 12, below. All six formulations contained 10 mM sodium phosphate buffer at pH 7.3

TABLE 12

Formulations for Long-Term Stability Assessment

| Formulation | % Sucrose (w/v) | % P188 (w/v) | Mannitol (mM) | NaCl (mM) | L-Arginine HCl (mM) |
|---|---|---|---|---|---|
| Placebo - 4 | 1.2 | 0.005 | 180 | 30 | 80 |
| Placebo - 7 | 5 | 0.005 | 180 | 30 | 80 |
| Placebo - 8 | 1.2 | 0.005 | 180 | 0 | 110 |
| rAAV - 4 | 1.2 | 0.005 | 180 | 30 | 80 |
| rAAV - 7 | 5 | 0.005 | 180 | 30 | 80 |
| rAAV - 8 | 1.2 | 0.005 | 180 | 0 | 110 |

The color and cake appearance of the lyophilized products were assessed by visual inspection, and the reconstitution time was determined as discussed above in Example 2. The results are shown in Table 13, below.

TABLE 13

Visual Appearance and Reconstitution Time

| Formulation | Cake Appearance | Recon Time (sec) | Post Recon Visual |
|---|---|---|---|
| Placebo - 4 | off-white uniform cake: no apparent reduction in volume or cake surface defects | 12 | Clear; free of visible particles |
| Placebo - 7 | off-white uniform cake: no apparent reduction in volume with slight shrinkage on the cake bottom | 15 | Clear; free of visible particles |
| Placebo - 8 | off-white uniform cake: no apparent reduction in volume or cake surface defects | 20 | Clear; free of visible particles |

TABLE 13-continued

| Formu-lation | Cake Appearance | Recon Time (sec) | Post Recon Visual |
|---|---|---|---|
| | _Visual Appearance and Reconstitution Time_ | | |
| rAAV - 4 | off-white uniform cake: no apparent reduction in volume | 13 | Clear; free of visible particles |
| rAAV - 7 | off-white uniform cake: no apparent reduction in volume with slight shrinkage on the cake bottom | 15 | Clear; free of visible particles |
| rAAV - 8 | off-white uniform cake: no apparent reduction in volume or cake surface defects | 15 | Clear; free of visible particles |

The average particle size to identify aggregates was determined both pre- and post-lyophilization, as discussed above in Example 3. The results are shown in Table 14, below.

TABLE 14

| Formulation | Z-Avg - DLS (Pre-Lyo) | Z-Avg - DLS (Post-Lyo) |
|---|---|---|
| | _Average Particle Size in Tested Formulations_ | |
| rAAV - 4 (sample 1) | 25.1 | 164.1 |
| rAAV - 7 (sample 1) | 24.7 | 36.5 |
| rAAV - 8 (sample 1) | 45.5 | 117.0 |
| rAAV - 4 (sample 2) | 25.1 | 164.6 |
| rAAV - 7 (sample 2) | 24.7 | 33.2 |
| rAAV - 8 (sample 2) | 40.5 | 115.7 |

Formulation rAAV-7, which demonstrated the best stability based on aggregation (Table 14), was further evaluated over a period of 6 months to monitor visual appearance, particle size, the % of full capsids, and the titer of the viral genome, as discussed above in Example 3. The results are shown below in Table 15.

TABLE 15

| Time point | Visual | DLS average size, nm | AEX % Full Capsid | ddPCR vg/mL |
|---|---|---|---|---|
| | _Lyophilized rAAV - 7 Stability at 5° C._ | | | |
| Pre lyophilized t = 0 | Elegant cake with no visible defects | 25 | 97 | 6.04E+12 |
| Post lyophilized t = 0 | Elegant cake with no visible defects | 35 | 96 | 5.48E+12 |
| Post Lyophilized 1 m | Elegant cake with no visible defects | 32 | 96 | 5.49E+12 |
| Post Lyophilized 3 m | Elegant cake with no visible defects | 37 | 96 | 5.73E+12 |
| Post Lyophilized 6 m | Elegant cake with no visible defects | 34 | 96 | 5.9E+12 |

The rAAV-7 (AAV8 serotype) showed good stability for up to six months at 5° C.

Figure 3:
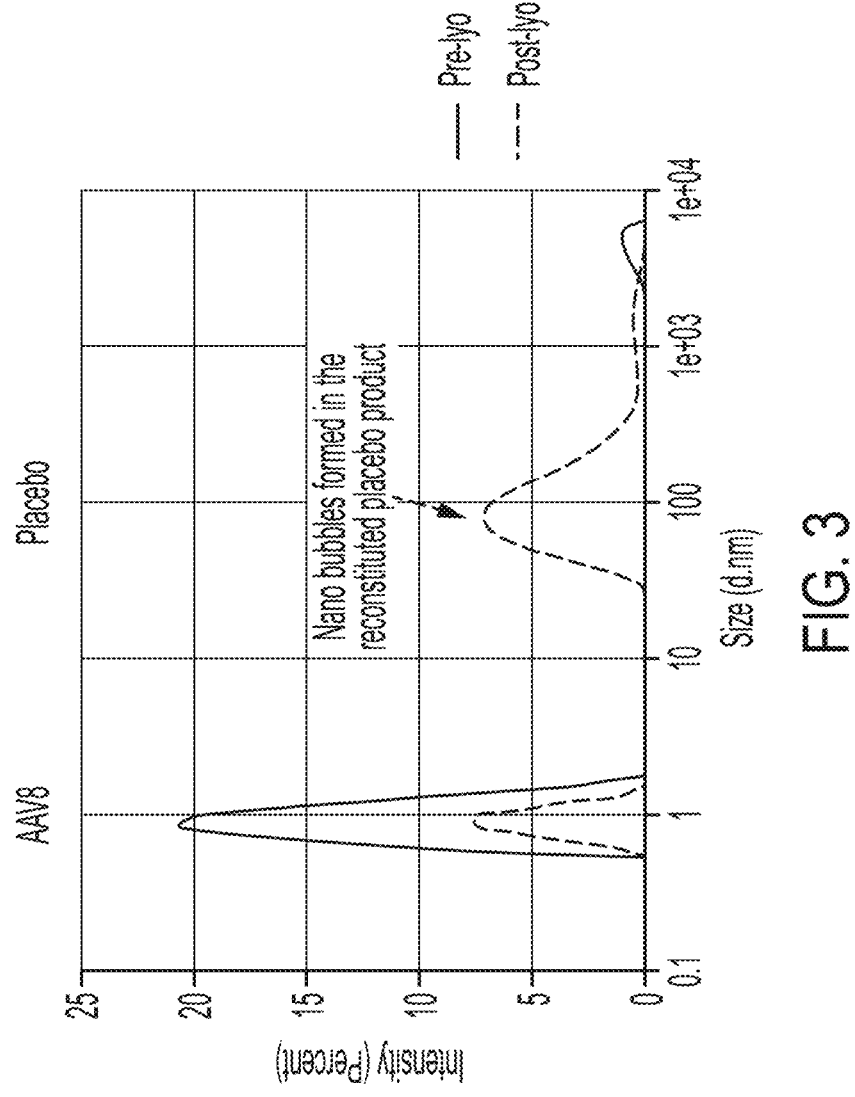
FIG. 3 shows a particle size comparison between AAV8 and a placebo formulation (without AAV) demonstrating the presence of nanobubbles in the reconstituted compositions.

As noted above in Examples 3 and 4, much of the observed increase in average particle size can be accounted for by the presence of nanobubbles in the reconstituted compositions. For example, although sample rAAV-7 demonstrated good post-lyophilization storage stability for AAV products, compared to the formulation prior to lyophilization, an approximately 10 nm increase in particle size was detected with DLS in the reconstituted rAAV-7 formulation upon completion of lyophilization (post-lyo t=0, Table 15), suggesting larger-size particle species were developed during the freeze-drying process. To investigate the root cause, a placebo sample (formulation without AAV particles) was lyophilized, and large particle species were identified with estimated sizes of approximately 100 to 200 nm (FIG. 3), in the same size range as the nanobubbles previously observed in reconstituted lyophilized protein products (data not shown), which likely arise from microvoids within the lyophilized cakes. Since no apparent particle size increase was detected post-lyophilization up to 6 months in the rAAV-7 formulation, the larger-size particle species developed during freeze-drying were likely due to nanobubbles instead of AAV aggregation. Moreover, the stability results from the lyophilized rAAV-7 formulation did not show any evidence suggesting the presence of nanobubbles in the freeze-dried cake had apparent adverse impact on AAV product storage stability.

Figures 7A, 7B, 7C:
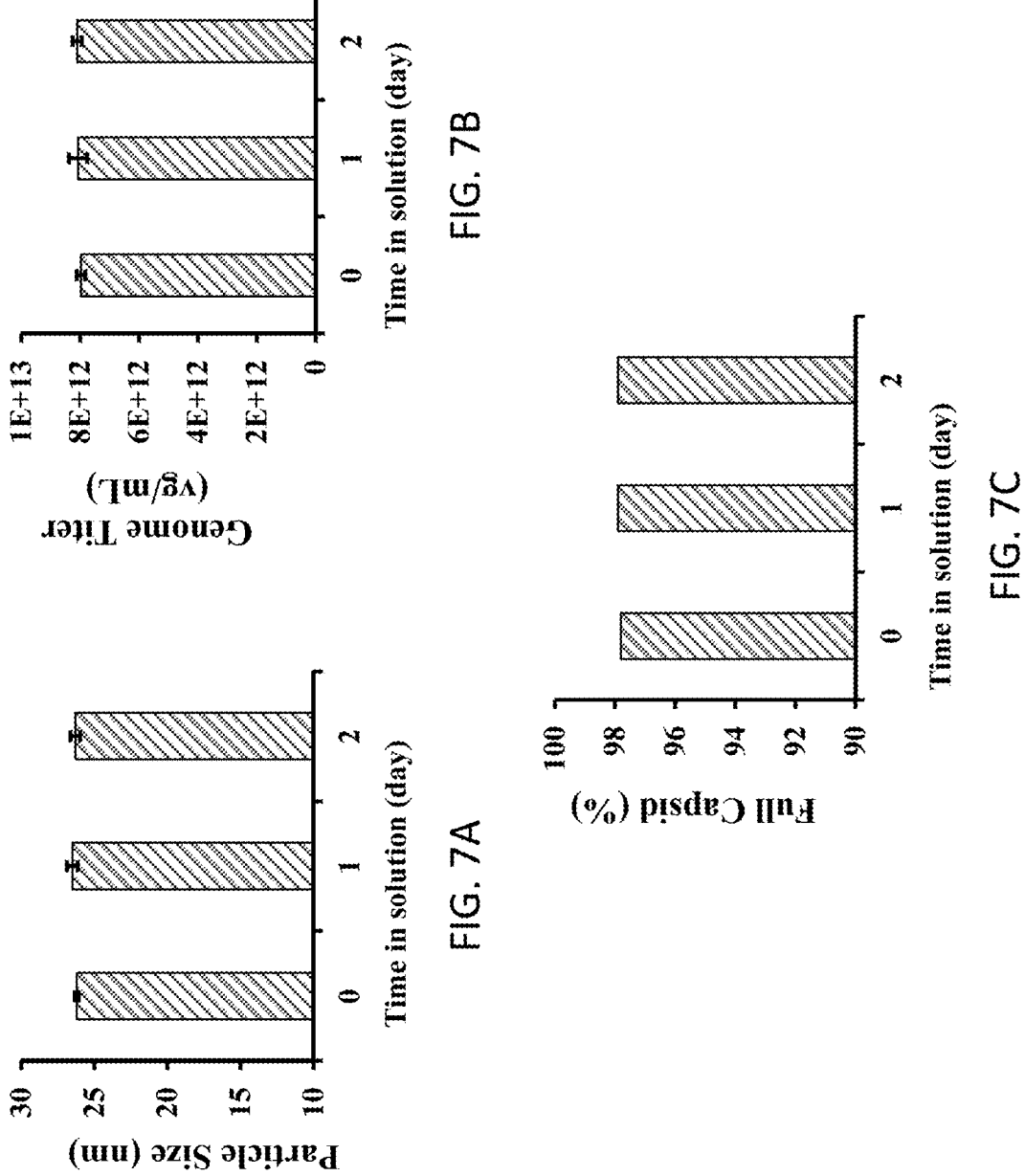
FIGS. 7A, 7B and 7C show in-solution stability results of an AAV8 formulation at 25° C. AAV8 vectors were formulated in F7 and stored at 25° C. for 2 days.

Example 8: Short-Term Stability of rAAV Lyophilized Formulations at Room Temperature At least 48 hours room temperature stability of the lyophilized formulation in the liquid state is desirable to support manufacturing operations such as hold steps prior to filling and dispensing the product into glass vials ahead of lyophilization. To evaluate the in-solution stability study, 0.7 mL of the AAV8 product in formulation F7 was filled in 2 mL type I glass vials and incubated at 25° C. for 2 days. As shown in FIGS. 7A, 7B and 7C, formulation F7 demonstrated good in-solution stability with no detectable changes in selected critical quality attributes (CQAs) for AAV including particle size by DLS for assessing aggregation, viral genome (vg) titer by ddPCR for assessing recovery, or empty to full capsid ratio by AEX for assessing capsid purity.

Another formulation containing AAV8 at $1 \times 10^{13}$ vg/mL, 10 mM tris, 30 mM sodium chloride, 80 mM L-arginine hydrochloride, 5% w/v sucrose, 3.3% w/v mannitol, and 0.01% w/v P188 at pH 7.3 was prepared, and evaluated for in-solution stability at 25° C. for 2 days, and for one month. Results are shown in FIGS. 10A, 10B and 100, and FIGS. 11A, 11B and 110, respectively. No significant changes were observed in CQAs including particle size, vg titer, and empty to full capsid ratio. The samples using cell-based potency assays and no significant changes were observed (data not shown).

Example 9: Long-Term Stability of rAAV Lyophilized Formulations at 2-8° C.

Figures 8A, 8B, 8C:
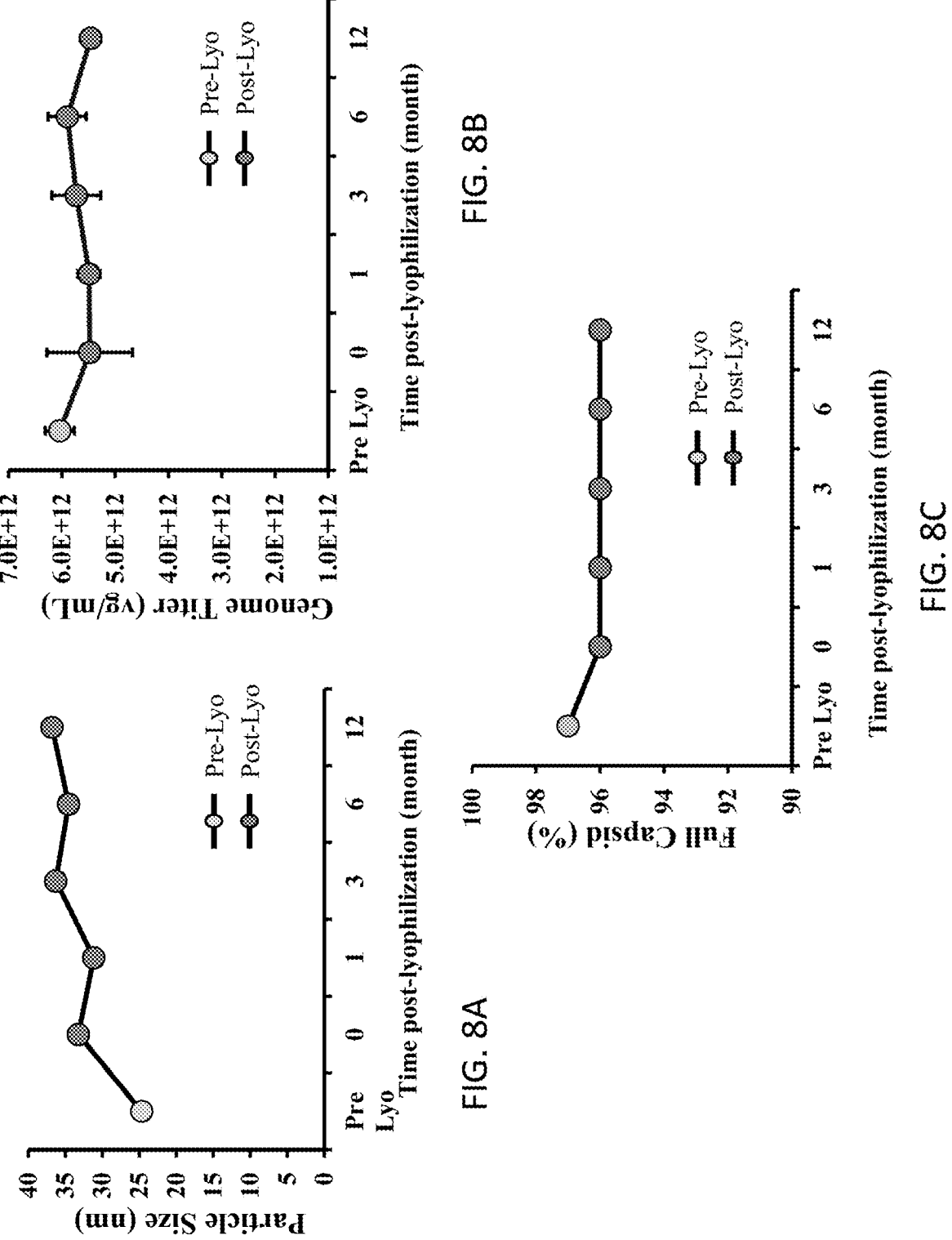
FIGS. 8A, 8B and 8C show results of storage stability of lyophilized AAV8 product in the F7 formulation at 2-8° C.

Long-term storage stability at 2-8° C. of lyophilized AAV8 drug product in formulation F7 was assessed at time 0, 1, 3, 6, and 12 months for cake appearance and reconstitution time (data not shown), as well as particle size, vg titer, and empty to full capsid ratio in the reconstituted AAV8 formulations. Results are shown in FIGS. 8A, 8B and 8C. No significant changes were observed for all the above assessments in post-lyophilization reconstituted formulations, indicating that the lyophilized AAV8 drug products in formulation F7 are stable during long-term storage at 2-8° C. for up to twelve months.

Compared to the pre-lyophilization time 0 sample, the approximately 10 nm increase in particle size by DLS in the post-lyophilization time 0 sample (FIG. 8A), can be attributed to nanobubbles, as discussed in Example 7. There is no evidence suggesting presence of nanobubbles significantly impacts the quality or stability of lyophilized protein products except for contributing to the numbers of submicron particles that can be detected in reconstituted lyophilized protein formulations.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A pharmaceutical formulation comprising:
(i) recombinant adeno-associated virus (rAAV) particles,
(ii) a buffering agent at a concentration of from about 5 mM to about 15 mM, wherein the buffering agent is a Tris buffer,
(iii) a first salt at a concentration of from about 20 mM to about 40 mM wherein the first salt is sodium chloride,
(iv) a second salt at a concentration of from about 30 mM to 90 mM, wherein the second salt is arginine hydrochloride,
(v) a sugar at a concentration of from about 1% w/v to about 5% w/v, wherein the sugar is sucrose,
(vi) a bulking agent at a concentration of from about 2% w/v to about 5% w/v, wherein the bulking agent is mannitol, and
(vii) a surfactant at a concentration of from about 0.001% w/v to about 0.1% w/v, wherein the formulation has a pH of from about 6.8 to about 7.8.

2. The pharmaceutical formulation of claim 1, wherein:
(a) the surfactant is a polysorbate or a poloxamer;
(b) the concentration of surfactant is from 0.001% w/v to 0.1% w/v; or
(c) the surfactant concentration is 0.01% w/v±0.005% w/v.

3. The pharmaceutical formulation of claim 1, wherein the pH of the formulation is from 7.0 to 7.6, or the pH of the formulation is 7.3±0.1.

4. The pharmaceutical formulation of claim 1, wherein the ratio of bulking agent to sugar is from 1:1 to 1:3, or wherein the bulking agent is mannitol, the sugar is sucrose, and the ratio of mannitol to sucrose is from 1:1 to 1:3.

5. The pharmaceutical formulation of claim 1, wherein the ratio of first salt to second salt is from 1:1 to 1:4.

6. The pharmaceutical formulation of claim 1, wherein the formulation has a total ionic strength of from 70 mM to 120 mM, or the formulation has a total ionic strength of 80 mM±5 mM or 110 mM±10 mM.

7. A pharmaceutical formulation comprising (i) recombinant adeno-associated virus (rAAV) particles at a concentration of from 1×10E10 vg/mL to 1×10E15 vg/mL, (ii) a phosphate buffer at a concentration of from 10 mM±1 mM, (iii) sodium chloride at a concentration of 30 mM±3 mM, (iv) L-arginine hydrochloride at a concentration of 80 mM±8 mM, (v) sucrose at a concentration of 5% w/v±0.5% w/v, (vi) mannitol at a concentration of 3.3% w/v±0.3% w/v, and (vii) poloxamer 188 at a concentration of 0.005% w/v±0.001% w/v, wherein the formulation has a pH of 7.3±0.2.

8. A pharmaceutical formulation comprising (i) recombinant adeno-associated virus (rAAV) particles at a concentration of from 1×10E10 vg/mL to 1×10E15 vg/mL, (ii) a Tris buffer at a concentration of 10 mM±1 mM, (iii) sodium chloride at a concentration of 30 mM±3 mM, (iv) L-arginine hydrochloride at a concentration of 80 mM±8 mM, (v) sucrose at a concentration of 5% w/v±0.5% w/v, (vi) mannitol at a concentration of 3.3% w/v±0.3% w/v, and (vii) poloxamer 188 at a concentration of 0.01% w/v±0.002% w/v, wherein the formulation has a pH of 7.3±0.2.

9. The pharmaceutical formulation of claim 1, wherein the rAAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S.

10. The pharmaceutical formulation of claim 1, wherein the formulation has an average particle size of from about 20 nm to about 40 nm, as determined by dynamic light scattering.

11. The pharmaceutical formulation of claim 1, wherein the formulation contains a collection of rAAV particles comprising at least 95% full capsids, as determined by anion-exchange chromatography.

12. A stable lyophilized pharmaceutical composition formed by lyophilizing the pharmaceutical formulation of claim 1.

13. The lyophilized pharmaceutical composition of claim 12, which:
(a) has a moisture content of 1.5% or less;
(b) has a moisture content of 1.0% or less;
(c) has a moisture content of from 0.5% to 0.8%, or 0.5%, 0.55%, 0.6%, 0.65%, 0.7%, 0.75%, or 0.8%;
(d) can be reconstituted in 30 seconds or less;
(e) can be reconstituted in 20 seconds or less; or
(f) can be reconstituted in 15 seconds or less.

14. A reconstituted drug product formed by reconstituting the lyophilized pharmaceutical composition of claim 12.

15. The reconstituted drug product of claim 14:
(a) comprising an average particle size of from about 20 nm to about 40 nm, as determined by dynamic light scattering;
(b) comprising a collection of rAAV particles comprising at least 95% full capsids, as determined by anion-exchange chromatography;
(c) comprising a collection of rAAV particles comprising a percentage of full capsids, as determined by anion-exchange chromatography, wherein the percentage of full capsids in the reconstituted drug product is within 2%, within 1%, or within 0.5% of a percentage of full capsids in the pharmaceutical formulation prior to lyophilization; or
(d) comprising a vector genome titer, as determined by droplet digital polymerase chain reaction, wherein the vector genome titer in the reconstituted drug product is within 10%, or within 7% of the vector genome titer present in the pharmaceutical formulation prior to lyophilization.

16. The reconstituted drug product of claim 15, formed by:
(a) reconstituting the lyophilized pharmaceutical composition after storage for 1 month at a temperature of from 2-8° C.;
(b) reconstituting the lyophilized pharmaceutical composition after storage for 3 months at a temperature of from 2-8° C.; or
(c) reconstituting the lyophilized pharmaceutical composition after storage for 6 months at a temperature of from 2-8° C.

17. A container containing the pharmaceutical formulation of claim 1.

18. A kit comprising the container of claim 17, and instructions for use.

19. A method of producing a stable lyophilized pharmaceutical composition, the method comprising performing a lyophilization process comprising (i) freezing, (ii) annealing, (iii), primary drying, and (iv) secondary drying on the pharmaceutical formulation of claim 1.

20. The method of claim 19, wherein:

(a) the freezing is performed at a temperature of −45° C.±5° C. for a period of 60 minutes±10 minutes;

(b) the freezing is performed both before and after the annealing;

(c) the annealing is performed at a temperature of −20° C.±5° C. for a period of 6 hours±30 minutes;

(d) the primary drying is performed at a temperature of −26° C.±5° C. for a period of 50 hours±10 hours; or (e) the secondary drying is performed at a temperature of 35° C.±5° C. for a period of from 5 to 20 hours, or a period of 15 hours±5 hours.

\* \* \* \* \*